US010603151B2

United States Patent
Barna et al.

(10) Patent No.: US 10,603,151 B2
(45) Date of Patent: Mar. 31, 2020

(54) MULTI-COMPONENT VAGINAL INSERT

(71) Applicant: Kimberly-Clark Worldwide, Inc., Neenah, WI (US)

(72) Inventors: Nicole J. Barna, Larsen, WI (US); Jeffrey L. Heinen, Neenah, WI (US); Yung Huang, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 96 days.

(21) Appl. No.: 16/112,968

(22) Filed: Aug. 27, 2018

(65) Prior Publication Data

US 2020/0060799 A1 Feb. 27, 2020

(51) Int. Cl.
*A61F 2/00* (2006.01)
*A61F 6/08* (2006.01)
*B29L 31/00* (2006.01)
*B29C 45/00* (2006.01)
*B29K 83/00* (2006.01)

(52) U.S. Cl.
CPC ............ *A61F 2/005* (2013.01); *A61F 2/0009* (2013.01); *A61F 6/08* (2013.01); *A61F 2240/001* (2013.01); *B29C 45/00* (2013.01); *B29K 2083/005* (2013.01); *B29L 2031/754* (2013.01)

(58) Field of Classification Search
CPC ........... A61F 2/005; A61F 6/08; A61F 2/0009
See application file for complete search history.

(56) References Cited

U.S. PATENT DOCUMENTS

| 4,307,716 | A | 12/1981 | Davis |
| 6,562,067 | B2 | 5/2003 | Mathis |
| 8,029,529 | B1 | 10/2011 | Chanduszko |
| 8,435,168 | B2 | 5/2013 | Ziv et al. |
| 8,617,047 | B2 | 12/2013 | Sinai et al. |
| 8,911,345 | B2 | 12/2014 | Ziv et al. |
| 8,993,641 | B2 | 3/2015 | Winn |
| 9,144,426 | B2 | 9/2015 | Ogdahl et al. |
| 9,173,768 | B2 | 11/2015 | Bartning et al. |
| 9,198,748 | B2 | 12/2015 | Ziv et al. |
| 9,339,363 | B2 | 5/2016 | Ziv et al. |
| 9,402,703 | B2 | 8/2016 | Ziv et al. |
| 9,675,437 | B2 | 6/2017 | Ziv et al. |
| 2009/0143489 | A1 | 6/2009 | Winn |
| 2010/0217068 | A1 | 8/2010 | Ziv et al. |
| 2011/0268676 | A1 | 11/2011 | Winn |
| 2015/0148421 | A1 | 5/2015 | Winn |
| 2015/0150671 | A1 | 6/2015 | Gilson et al. |
| 2015/0173875 | A1 | 6/2015 | Romzek et al. |
| 2016/0256250 | A1 | 9/2016 | Cestari |

OTHER PUBLICATIONS

"Poise—What Are Poise* Impressa* Bladder Supports Made Of?", http://www.poise.com/products/impressa/faq/whatarepoiseimpressabladdersupportsmadeof, Sep. 30, 2016.

*Primary Examiner* — Christine H Matthews
(74) *Attorney, Agent, or Firm* — Kimberly-Clark Worldwide, Inc.

(57) ABSTRACT

A vaginal insert which can be provided in an applicator for the treatment of urinary incontinence in females. The vaginal insert can provide tension-free incontinence treating support perpendicularly to the urethra (i.e., across the urethra).

11 Claims, 24 Drawing Sheets

|  | SIZE 1 | SIZE 2 | SIZE 3 | SIZE 4 |
|---|---|---|---|---|
| HORIZONTAL ROTATION (Lt/Rt) | +/-17 | +/-20 | +/-22 | +/-25 |
| MEDIAL DEFLECTION | +0-24 | +0-29 | +0-34 | +0-38 |

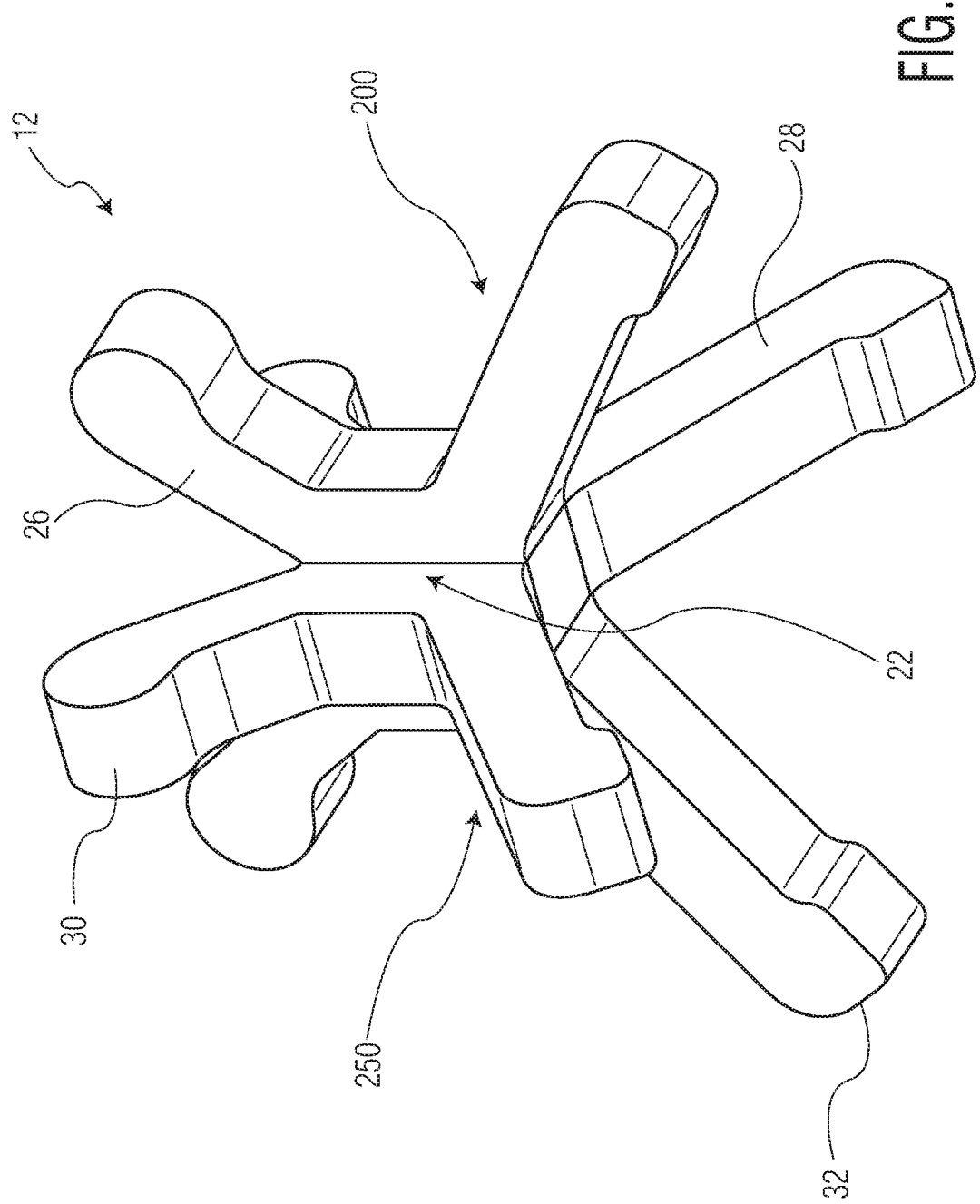

| CORE DIMENSIONS | | | | | | | |
|---|---|---|---|---|---|---|---|
| | DIAMETER OF ANCHORING ELEMENT [mm] | | DIAMETER OF SUPPORTING ELEMENT [mm] | | CORE LENGTH [mm] | | WEIGHT [gr] |
| SIZE | | | | | | | |
| SIZE-1 | 30.8 | 32.8 | 35 | 37 | 42.3 | 44.3 | 5.9 6.3 |
| SIZE-2 | 30.8 | 32.8 | 40 | 42 | 40.7 | 42.7 | 5.9 6.3 |
| SIZE-3 | 30.8 | 32.8 | 45 | 47 | 38.5 | 40.5 | 5.9 6.3 |
| SIZE-4 | 30.8 | 32.8 | 49 | 51 | 36.7 | 39 | 5.9 6.3 |

FIG. 15A

| | PULLING STRING LENGTH [cm] | DIAMETER OF SUPPORTING ELEMENT | | |
|---|---|---|---|---|
| | | [mm] | ± TOLERANCE [mm] | [mm] |
| 1 | 12-16 | 34 | 35.75±1.75 | 37.5 |
| 2 | 12-16 | 38 | 39.5±1.5 | 41 |
| 3 | 12-16 | 43.5 | 45.0±1.5 | 46.5 |
| 4 | 12-16 | 47.5 | 49.0±1.5 | 50.5 |

FIG. 15B

| MATERIAL | S70 | | | S50 | | | S40 | | |
|---|---|---|---|---|---|---|---|---|---|
| SLOPE | MIN | MID | MAX | MIN | MID | MAX | MIN | MID | MAX |
| SIZE 1 | 6.90 | 7.70 | 8.50 | 2.80 | 3.15 | 3.50 | 2.20 | 2.50 | 2.80 |
| SIZE 2 | 6.30 | 7.10 | 7.90 | 2.80 | 3.15 | 3.50 | 2.20 | 2.50 | 2.80 |
| SIZE 3 | 5.60 | 6.15 | 6.70 | 2.50 | 2.75 | 3.00 | 1.60 | 1.90 | 2.20 |
| SIZE 4 | 5.00 | 5.85 | 6.70 | 2.50 | 2.75 | 3.00 | 1.60 | 1.90 | 2.20 |

FIG. 15C

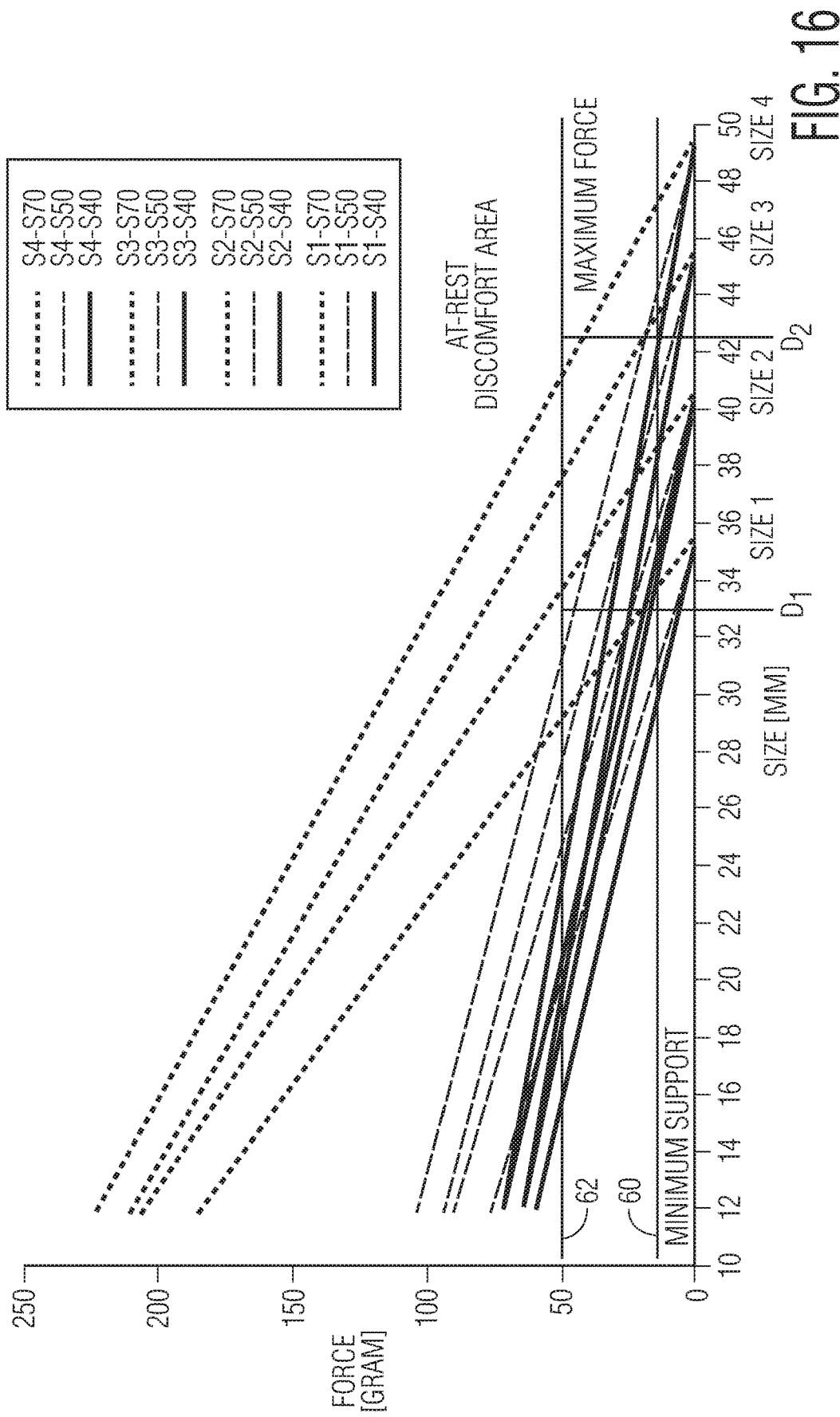

| MATERIAL | SIZE | NOMINAL DIAMETER | SLOPE | MINIMAL DIAMETER | MAX FORCE |
|---|---|---|---|---|---|
| S40 | 1 | 36 | 2.5 | 12.0 | 60.0 |
|  | 2 | 41 | 2.5 | 12.0 | 72.5 |
|  | 3 | 46 | 1.9 | 12.0 | 64.6 |
|  | 4 | 50 | 1.9 | 12.0 | 72.2 |
| S50 | 1 | 36 | 3.15 | 12.0 | 75.6 |
|  | 2 | 41 | 3.15 | 12.0 | 91.4 |
|  | 3 | 46 | 2.75 | 12.0 | 93.5 |
|  | 4 | 50 | 2.75 | 12.0 | 104.5 |
| S70 | 1 | 36 | 7.7 | 12.0 | 184.8 |
|  | 2 | 41 | 7.1 | 12.0 | 205.9 |
|  | 3 | 46 | 6.15 | 12.0 | 209.1 |
|  | 4 | 50 | 5.85 | 12.0 | 222.3 |

FIG. 17

MULTI-COMPONENT VAGINAL INSERT

BACKGROUND OF THE DISCLOSURE

Urinary incontinence is a problem among females. It is estimated that up to 50% of women occasionally leak urine involuntarily and that approximately 25% of women will seek medical advice in order to deal with the problem. Stress incontinence, the most common type of urinary incontinence, refers to the involuntary leakage of urine resulting from a rise in abdominal pressure. When involuntary urination occurs, it often happens because of a rise in pressure in the bladder for which there is no compensating counter-pressure from the bladder neck or urethra. This is usually the result of the abnormal descent of the bladder neck and the urethra into a low position and away from the intra-abdominal pressure system. Known as "hypermobility," this can be the result of some injury to the support mechanism which normally keeps the urethra and the bladder neck in a raised position along the backside of the pubic bone.

The lowering of the bladder neck and the urethra that occur, for example, when a woman coughs, sneezes, or laughs, can cause involuntary leakage of urine. While many different factors may contribute to the development of stress incontinence, it is most prevalent among women ages 35-65 and those who have had multiple vaginal deliveries.

Stress incontinence is both aggravating and unpleasant for women and it can also be embarrassing. Many women wear sanitary pads in order to deal with stress incontinence although this is not a real solution to the problem and it can be very inconvenient and unreliable. Surgical treatment may involve, among other things, elevation of the anterior vaginal wall (Anterior Colporrhaphy), securing the paraurethral tissues to the periosteum of the pubic bone (Marshall-Marchetti-Krantz operation), or elevation of the paracervical vaginal anterior wall to the Coopers ligament (Burch colpo suspension) in order to elevate the bladder neck above the level of the pelvic floor and thereby distribute pressure equally to the bladder, the bladder neck, and the mid-urethra. Recently, a procedure known as "TVT" (Tension Free Vaginal Tape) was developed in which a mesh tape is implanted underneath the urethra (usually mid-urethra) creating a hammock on which the urethra may kink during a rise in intra-abdominal pressure. However, surgery is only suitable for severe cases and the majority of women experiencing stress incontinence do not need, and certainly would rather avoid, surgical solutions.

One non-surgical treatment involves the use of vaginal inserts that are inserted into the vagina either by a medical practitioner or by the woman herself. Most vaginal inserts are designed to apply pressure against the bladder neck so as to inhibit or completely block the flow of urine through the urethra. One problem with such vaginal inserts is that they completely block the urethra and thus they need to be removed or collapsed in order to allow the woman to urinate. To overcome this drawback vaginal inserts have been developed having specialized shapes that do not completely block the urethra but these vaginal inserts tend to be large, uncomfortable, and intrusive. They also tend to cause irritation or soreness to the vagina.

Another common shortcoming is that most vaginal inserts also tend to be difficult, painful, or uncomfortable to insert and/or remove. In order to correctly inhibit urine flow, the vaginal insert needs to be properly positioned in the vaginal canal. As a result, a doctor may be required to properly position the vaginal insert. In most cases, the vaginal insert is adapted for remaining in the vagina for a prolonged period of time (due to the time and expense of requiring a trained medical professional to insert and/or remove the vaginal insert). However, when positioned in the vagina for an extended period of time, the vaginal insert may cause vaginal infections, pressure ulcers, and/or bleeding.

A woman may desire to insert a vaginal insert herself thereby asserting personal control over the insertion and removal of the vaginal insert. To assist with the insertion of the vaginal insert, an applicator, such as is used for tampon insertion, can be provided to house the vaginal insert. A shortcoming associated with simply placing the vaginal insert into an applicator is that the vaginal insert can experience migration towards the outlet of the applicator, such as during shipment or storage. If the vaginal insert migrates too far towards the outlet, the vaginal insert may self-expel from the applicator prematurely.

A vaginal insert for treating urinary incontinence should have a size and shape configuration such that it can be comfortable during the insertion and removal process. A vaginal insert for treating urinary incontinence also needs to be capable of expanding following insertion into the vagina and during wear in order to provide efficacious incontinence protection. A vaginal insert for treating urinary incontinence also needs to be cost effective to manufacture in order to provide a woman with a cost effective treatment. For example, currently available vaginal inserts may be manufactured via a molding process. A vaginal insert having a specialized shape so as to not completely block the urethra may require a complex mold and molding process to manufacture the vaginal insert. There is a need for a vaginal insert which can be manufactured utilizing a simplified manufacturing process. There is a need for a vaginal insert for treating urinary incontinence which can be comfortable to wear in an at-rest state and which can provide incontinence prevention during a high stress event. There is a need for a vaginal insert which can be inserted by the woman without the need for a trained medical professional. There is a need for a vaginal insert which can be provided to a woman in an applicator. There is a need for a vaginal insert which can remain in the applicator until such a time when the vaginal insert is needed by the woman.

SUMMARY OF THE DISCLOSURE

In various embodiments, a vaginal insert can have a core, the core can have a first component having a first major surface and a second major surface separated from the first major surface by a first thickness; a first anchoring arm and a second anchoring arm; a first supporting arm and a second supporting arm; a first intermediate region separating the first and second anchoring arms from the first and second supporting arms; and a first groove within the first intermediate region, the first groove extending between and connecting the first and second anchoring arms; a first edge proximal to a junction between the first groove and the first anchoring arm; a second edge proximal to a junction between the first groove and the second anchoring arm; a first width dimension between the first edge and the second edge; a second component having a third major surface and a fourth major surface separated from the third major surface by a second thickness; a third anchoring arm and a second anchoring arm; a third supporting arm and a second supporting arm; a second intermediate region separating the third and fourth anchoring arms from the third and fourth supporting arms; and a second groove within the second intermediate region, the second groove extending between and connecting the third and fourth supporting arm; a third edge proximal to a junction between the second groove and the third supporting arm; a fourth edge proximal to a junction between the second groove and the fourth supporting arm; a second width dimension between the third edge and the fourth edge; wherein the first intermediate region of the first component fits within the second groove of the second component and the second intermediate region of the second component fits within the first groove of the first component, and wherein the first width dimension is smaller than the second thickness and the second width dimension is smaller than the first thickness.

In various embodiments, the first width dimension is from 10% to 90% smaller than the second thickness. In various embodiments, the second width dimension is from 10% to 90% smaller than the first thickness.

In various embodiments, the vaginal insert further has a cover. In various embodiments, the vaginal insert further has a removal element.

In various embodiments, the core further comprises a first migration reduction feature located on the first supporting arm of the first component. In various embodiments, the first migration reduction feature is located on an applicator facing surface of the first supporting arm of the first component. In various embodiments, the first migration reduction feature is located on a non-applicator facing surface of the first supporting arm of the first component. In various embodiments, the vaginal insert further has a second migration reduction feature located on an applicator facing surface of the first supporting arm of the first component. In various embodiments, the vaginal insert further has a second migration reduction feature located on a non-applicator facing surface of the first supporting arm of the first component. In various embodiments, the vaginal insert further has a second migration reduction feature located on a second supporting arm of the first component.

BRIEF DESCRIPTION OF DRAWINGS

FIG. 10C is an exemplary embodiment of a core formed from the components illustrated in FIGS. 10A and 10B.

FIGS. 15A-15C are a series of charts illustrating exemplary core specifications.

FIG. 16 is a vaginal insert performance graph correlating force exerted to core size, diameter, and hardness.

FIG. 17 is a table showing performance characteristics for exemplary basic core configurations.

Figure 1:
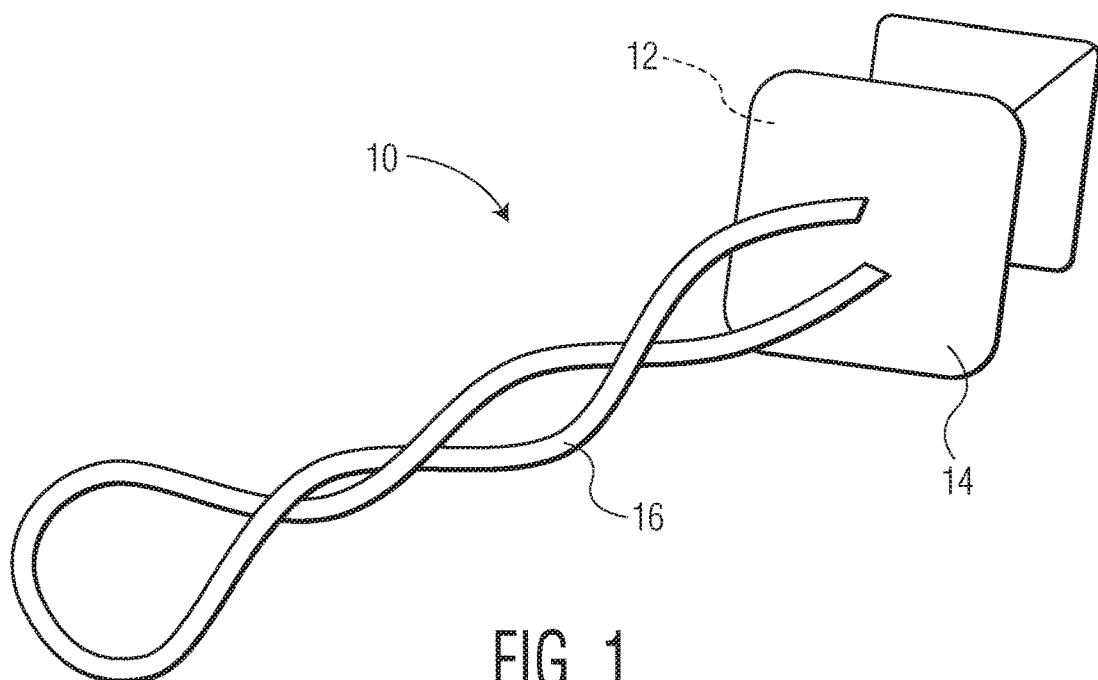
FIG. 1 is a perspective view of an exemplary embodiment of a vaginal insert.

Repeat use of reference characters in the present specification and drawings is intended to represent the same or analogous features or elements of the disclosure.

DETAILED DESCRIPTION OF THE DISCLOSURE

The present disclosure is generally directed towards a vaginal insert which can be provided in an applicator for the treatment of urinary incontinence in females. The vaginal insert can provide tension-free incontinence treating support perpendicularly to the urethra (i.e., across the urethra). It should also be noted that for some women, the described vaginal inserts can also be used as a treatment or part of a treatment for prolapse.

In various embodiments, the vaginal insert can be adapted to be stable in the vagina without significant longitudinal and/or rotational movement within the vagina. For example, supporting and anchoring arms of the vaginal insert can be designed to resist longitudinal movement within the vagina. As another example, the tips of the supporting and/or anchoring arms can be designed to resist rotational motion by working with the natural behavior of the vaginal wall to at least partially envelope the tip, thereby preventing rotational movement. Stability can also be enhanced by using the supporting and/or anchoring arms to provide contact between the vaginal insert and multiple points located spatially around the vaginal insert on the vaginal wall. In an embodiment, proper support-rendering positioning of the vaginal insert can be considered to be where two supporting arms position themselves one on each side of the urethra while at least one other supporting arm provides opposing force to the vaginal insert when the two supporting arms are subjected to force from the urethra during high-stress events that cause the urethra to drop in the vagina.

In various embodiments, the vaginal insert can be adapted to be disposable, worn only for a relatively short period of time and then discarded and replaced with a new vaginal insert (if needed). Alternatively, the vaginal insert can be recycled for use by sterilizing it between uses. The vaginal insert can be simple and easy to use and can be inserted in the same user-friendly manner that a tampon is inserted into the vagina during menstruation, for example by using an applicator. In an embodiment, the vaginal insert can be inserted in any orientation since the vaginal insert can naturally migrate into a correct treatment position as a result of the vaginal insert geometry. The vaginal insert can be small, exemplary sizes described below, comfortable, and once inserted, the woman need not think about it again until it is removed. As with insertion, removal can be accomplished in a similar manner as a tampon, such as by pulling on a removal element.

In various embodiments, the vaginal insert can include a core and a removal element. In various embodiments, the vaginal insert can include a core, a cover, and a removal element. Each of these components will be described in more detail below. An example of a vaginal insert 10 having a core 12, a cover 14, and a removal element 16 can be seen in FIG. 1.

Figure 2:
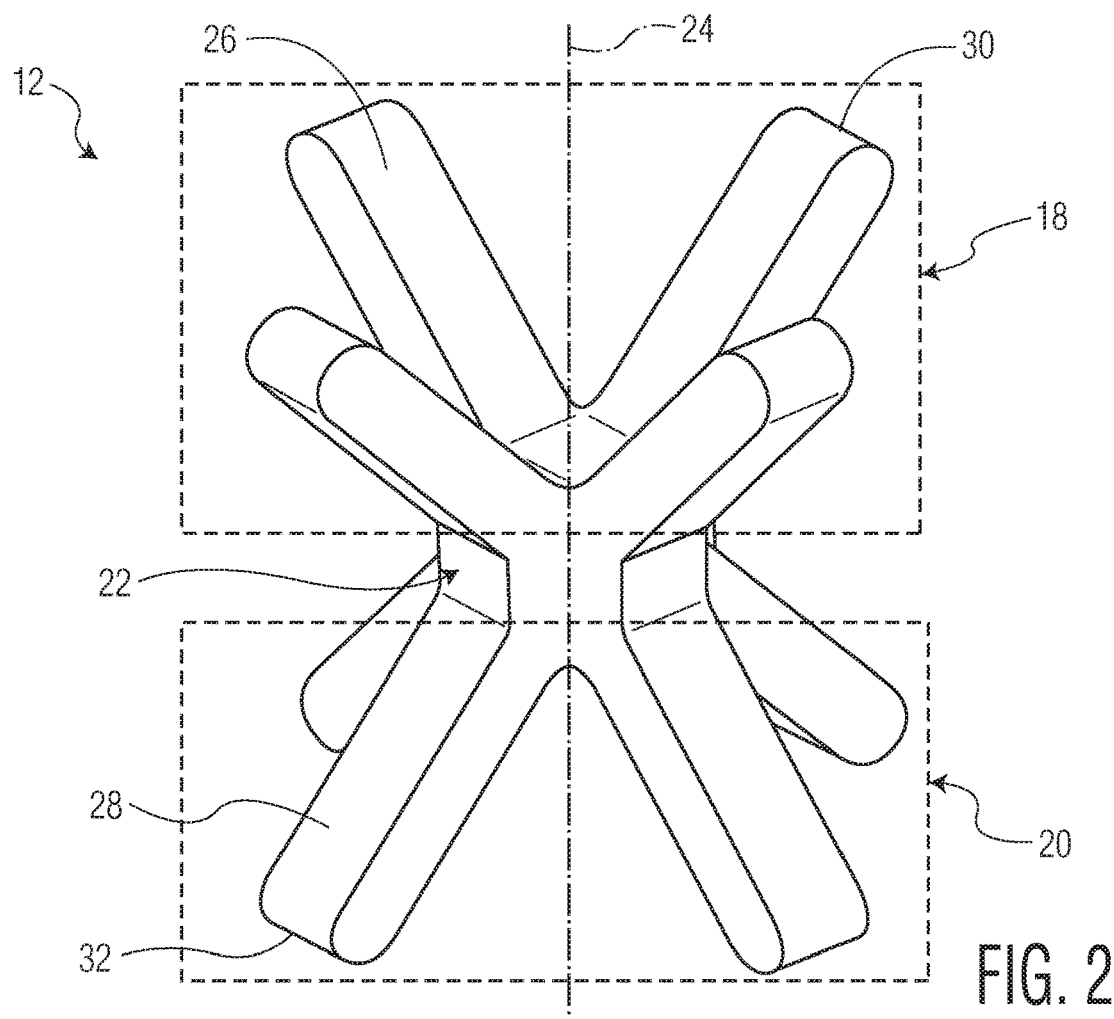
FIGS. 2-4 are perspective views of exemplary embodiments of a core.
Figure 3:
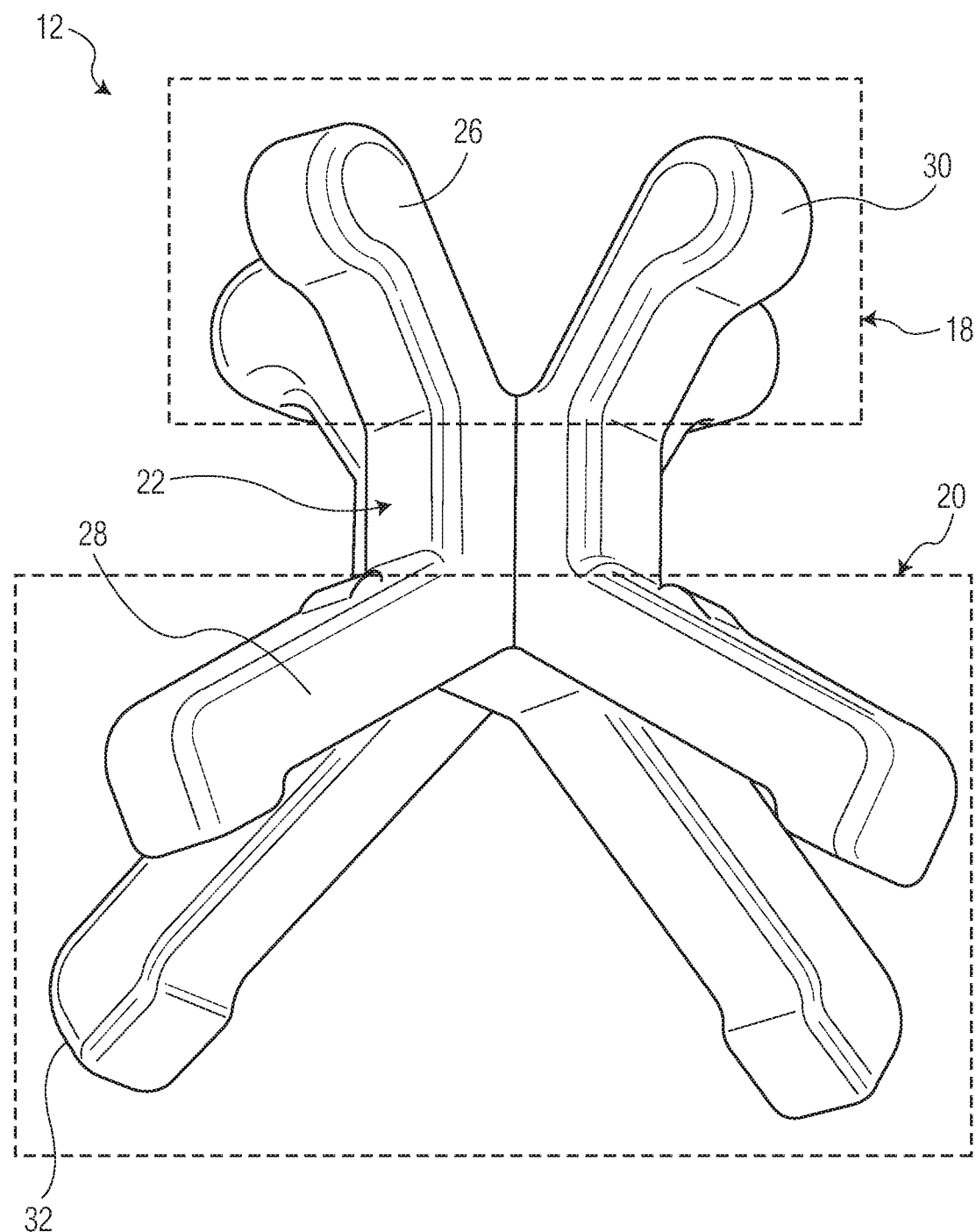

Referring to FIGS. 2 and 3, exemplary embodiments of a core 12 for a vaginal insert 10 (illustrated in FIG. 1) for treating urinary incontinence are illustrated. For ease of description, the core 12 can be arranged around a longitudinal axis 24 and divided into three basic elements. A top section 18 can be provided which can serve as the "anchoring" element for stabilizing the vaginal insert 10 within the vagina. There can be at least one of three types of anchoring: axial anchoring which can act in the direction along the central axis of the vagina, radial anchoring which can act side-to-side or substantially perpendicular to the central axis of the vagina, and/or rotational anchoring which will be described in more detail below. In an embodiment, the anchoring element 18 does not apply significant pressure to the wearer's vagina and/or urethra, which can thereby result in enhanced comfort. A bottom section 20 can be provided which can serve as the "supporting" element for generating support. In various embodiments, support can be generated at a sub-urethral location, for example mid-urethra. Alternatively, additionally, and/or optionally, support can be generated at the bladder neck. In various embodiments, the supporting element 20 can provide at least one type of anchoring, described above, to help anchor the vaginal insert 10 in position within the vagina. In various embodiments, the roles of anchoring 18 and supporting 20 elements can be switched or shared. In an embodiment, the anchoring 18 and supporting 20 elements of the core 12 can function as an internal support structure for a cover 14 (such as illustrated in FIG. 1).

In an embodiment, an intermediate section can be provided which can act as a "node" 22 and which can connect anchoring 18 and supporting 20 elements. The node 22 of core 12 can have a length which can be a small portion of the overall length of the core 12. In various embodiments, the length of the node 22 can be less than about 15, 20, or 30% of the entire length of the core 12. In various embodiments, a node 22 having a short length relative to the entire length of the core 12 can allow for more flexibility in varying the stiffness, the comfort, and the size of the core 12 when compared with a same length core 12 with a longer node 22.

Various design aspects of the core 12 can encourage stability of the vaginal insert 10 in the vagina, including: the longitudinal design of the core 12 which can incorporate anchoring arms 26 adapted to prevent movement of the vaginal insert 10 deeper into the vagina and/or supporting arms 28 adapted to prevent movement of the vaginal insert 10 towards the entrance to the vagina; specially adapted arm tips, such as tips 30 and 32, which can resist rotational movement of the vaginal insert 10 as they can be at least partially enveloped by the vaginal wall; an overall design which can take advantage of the vaginal tenting phenomenon; and, a multi-dimensional aspect which can allow various arms, 26 and/or 28, of the core 12 to contact multiple and/or opposing vaginal surfaces concurrently.

In an exemplary embodiment, the anchoring element 18 and the supporting element 20 can each have four arms, 26 and 28, respectively. In such an exemplary embodiment, two arms, 26 and 28, of each of the anchoring 18 and supporting 20 elements, respectively, can generally exert pressure towards the anterior vaginal wall and two arms, 26 and 28, of each of the anchoring 18 and supporting 20 elements, respectively, can generally exert pressure towards the posterior vaginal wall adjacent the bowels. The distal part of the urethra extends into the vagina forming a natural recess between the urethral bulge and the vaginal wall. The arms, 26 and/or 28, which exert pressure anteriorly can fit within these natural recesses on either side of the urethra. In various embodiments, the anchoring element 18 and the supporting element 20 can each have more or less arms, 26 and 28, respectively. For example, the anchoring element 18 could have more anchoring arms 26 if there is a concern about unwanted movement of the vaginal insert 10.

Supporting arms 28 can cause elevation of the tissues around the urethra, optionally mid-urethra and/or bladder neck thereby acting as a hammock. This hammock can support the urethra in a tension free manner. In a woman who leaks urine during a stress event (e.g., when abdominal pressure rises during coughing, sneezing, etc.), the urethra sags down but meets the hammock in its mid-part. The meeting of the urethra and the hammock can cause an elevation of the intra-urethral pressure with resultant urinary continence.

In an embodiment, anchoring arms 26 can force the vaginal insert 10 to remain in situ within the vagina, unable to substantially move inwards or outwards of the vagina, or to rotate within the vagina. One reason that this can occur can be as a result of the tendency of vaginal walls to collapse and form an occluded lumen. The arms, 26 and 28, of the core 12 can cause "tenting" of the vaginal walls on top of the arms with resultant sagging of the vaginal walls around the core 12, which can thereby stabilize the core 12. Additionally, in various embodiments, anchoring arms 26 can be flexible and/or elastic and/or resilient. This flexibility can enhance the anchoring arms 26 ability to prevent motion of the vaginal insert 10 further into the vagina. As force strives to exert itself on the vaginal insert 10 and move the vaginal insert 10 further into the vagina, the flexible anchoring arms 26 can tend to spread apart. This spreading action of the anchoring arms 26 can increase the friction between the vaginal insert 10 and the vaginal wall, thereby preventing movement further into the vagina. While the anchoring arms 26 can be flexible, it should be noted that they can be rigid enough and/or can be configured to spread to prevent unwanted motion of the vaginal insert 10 towards the entrance of the vagina. In an embodiment, the anchoring arms 26 can be rigid but the node 22 can be flexible allowing the node 22 to provide flexible anchoring support. Movement towards the vaginal opening can also be resisted by the supporting arms 28 which tend to widen radially when pulled outwardly. These features work with the tenting behavior of the vaginal walls which also helps to maintain the vaginal insert 10 in place.

The anchoring arms 26 can have tips 30 and the supporting arms 28 can have tips 32. In various embodiments, the tips 30 of the anchoring arms 26 can be rounded or spherical in nature, to provide smooth surfaces (i.e., no corners or points) for the tenting of the vaginal wall. In various embodiments, the tips 32 of the supporting arms 28 and/or corners of the core 12 can be blunted by a beveled edge along the anchoring arms 26 and supporting arms 30 and at the tips 32. In various embodiments, the tips 32 can be slightly rounded and/or have a beveled edge. In various embodiments, the beveled edge of the supporting arms 28 can reduce the overall circumference of the core 12, relative to a completely spherical cross section, when it is in a compressed mode for packaging within an applicator.

In various embodiments, cores 12 of all sizes can have arms, both anchoring 26 and supporting 28 arms, which can be the same length, such as, for example, illustrated in FIG. 2. In such embodiments, the core 12 can be symmetrical about the longitudinal axis 24 of the core 12 as well as symmetrical about the lateral axis of the core 12 wherein the lateral axis of the core 12 can be located at the midpoint of the longitudinal axis 24. In various embodiments, the node 22 can be located at the midpoint of the longitudinal axis 24. In various embodiments, core 12 of all sizes can have the same total length when completely compressed inwardly. In various embodiments, anchoring arms 26 can be shorter than the supporting arms 28, such as, for example, illustrated in FIG. 3. In such embodiments, the longitudinal length of the anchoring element 18 can be shorter than the longitudinal length of the supporting element 20 when the core 12 has been completely inwardly compressed. An example of an inwardly compressed core 12 in which the anchoring element 18 is shorter than the supporting element 20 can be seen in FIG. 4. In such an embodiment, the node 22 is not necessarily located at the midpoint of the longitudinal axis 24. In such an embodiment, the core 12 may be symmetrical about the longitudinal axis 24, however, the core 12 is not necessarily symmetrical about the lateral axis which can be located at the midpoint of the longitudinal axis. In an embodiment, anchoring arms 26 can be a consistent size in a line-up of different sizes of cores 12 even though the supporting arms 28 may vary in size and/or performance. Anchoring arms 26 can be the same size, in various embodiments, to ease manufacturing considerations. In various embodiments, the anchoring arms 26 of the core 12 can operate independently, relative to the longitudinal axis of the vagina, from the supporting arms 28.

In various embodiments, the difference between sizes of cores 12 can be the resting angle at which supporting arms 28 protrude outwardly relative to the longitudinal axis 24 of the core 12. In various embodiments, "larger" size cores 12 can have a larger radial spread angle of supporting arms 28, hence they can be "shorter" when put next to a smaller size core 12 (i.e., a core 12 which does not radially spread its supporting arms 28 as much). One potential advantage for such a design can be that all cores 12, no matter the radial spread angle, can be inserted into one size of an applicator 40.

In an embodiment, the flexibility of various components of the core 12 of a vaginal insert 10 can be designed both for function and for comfort to the user. In various embodiments, the core 12 of a vaginal insert 10 can be designed with at least one of four aspects of flexibility which can assist in accomplishing these goals of function and comfort. For example, node 22 of core 12 can enable flexibility between the anchoring element 18 and the supporting element 20, which can enable the vaginal insert 10 to adjust to the arch structure of the vagina, as well as to adjust to any position taken by the wearer (e.g., standing, sitting, flexion, etc.) during daily activity. By being able to flex at the node 22, pressure exerted on the vaginal wall can be reduced in relation to a vaginal insert 10 that does not flex at the node 22.

Figures 5, 6:
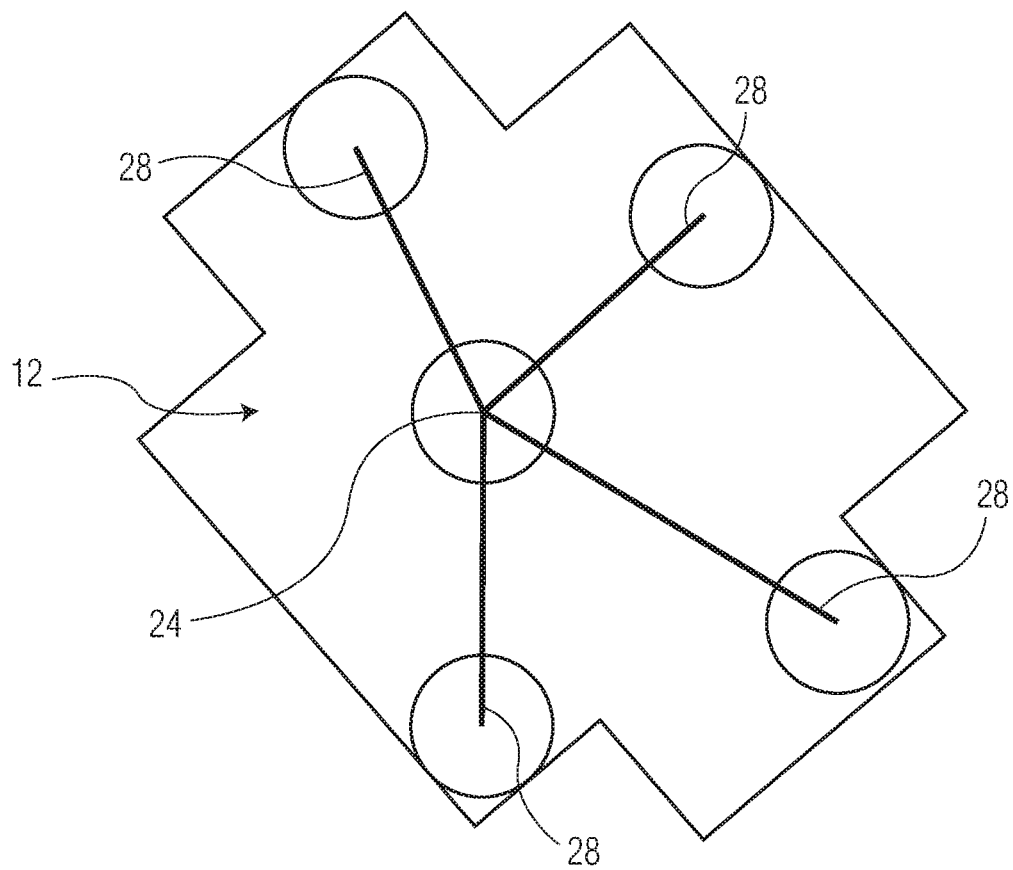
FIG. 5 is a plan view of an exemplary embodiment of a possible relationship of the supporting arms of a core to the longitudinal axis of the core.
FIG. 6 is a table showing exemplary performance ranges for medial deflection and horizontal rotation (left/right from the central axis), in accordance with an exemplary embodiment of the core.

Another flexibility aspect of the core 12 can relate to providing efficacy and comfort across varying vaginal planes, for example where the arms, 26 and/or 28, are adapted to contact the vaginal wall at varying locations and/or angles of incidence, relative to each other, away from the longitudinal axis 24, such as shown in FIG. 5, which can allow the core 12 of the vaginal insert 10 to be adaptable to varying vaginal topography/geometries by rotating either left or right from the central axis of each arm.

Another related aspect of flexibility can involve the ability of each of the arms, 26 and/or 28, to perform medial flexion, wherein each arm, 26 and/or 28, can be flexible towards the longitudinal axis 24 when compressed by the vaginal wall, enabling the adjustment of the vaginal insert 10 to various vaginal diameters.

A fourth flexibility aspect can be the feature that each arm, 26 and/or 28, can operate individually, for example, each arm, 26 and/or 28, being able to twist clockwise and/or counterclockwise around its own axis allowing the core 12 of the vaginal insert 10 to overcome vaginal structural variability from one point of contact to the next.

It should be noted that in various embodiments, at least one of these four featured aspects of flexibility can allow the core 12 of the vaginal insert 10 to render the effective support regardless of vaginal dimension, vaginal shape, vaginal depth, and/or through multiple planes.

FIG. 6 is a table showing exemplary performance ranges for medial deflection (distance the tip of an arm or arms travel toward the longitudinal axis 24 of the core 12) and horizontal rotation (left/right movement perpendicular to the longitudinal axis 24), in accordance with an exemplary embodiment of a core 12. Numbers shown are in millimeters. It should be understood that horizontal rotation means rotation in axes perpendicular to the longitudinal axis of the vagina, particularly "right" and "left" when viewing the vagina in the longitudinal axis extending from the vaginal opening to the cervix. The ranges shown in FIG. 6 are amounts in mm that each arm could deviate from its natural position relative to the longitudinal axis 24 of the core 12. Regarding medial deflection, it should be noted that when an arm is deflected medially, there is most often a corresponding arm on the other side of the core 12 which is also deflected medially (but maybe not the same amount), therefore, in an embodiment, medial deflection numbers (in mm) are divided by two in order to approximate medial deflection for a single arm. It should also be noted that the numbers for medial deflection in that table in FIG. 6 represent the full amount of deflection for a single arm assuming the corresponding arm does not move at all. In addition, in some embodiments, the maximum amount of medial deflection is dictated by two opposing arms contacting each other, preventing further medial deflection. In various embodiments, the minimum core 12 diameter that can be achieved is 12 mm, with each arm representing a 6 mm portion of that total.

In various embodiments, the core 12 can be made in a plurality of sizes and/or made to exhibit specific performance characteristics, such as radial expansion of the supporting arms 28. In various embodiments, the diameter of a radially expanded anchoring element 18 can range from about 30 to about 33 mm. In various embodiments, the diameter of a radially expanded supporting element 20 can range from about 34 or 41 mm to about 50, 51, or 52 mm. In various embodiments, the core 12 can have a length in an expanded configuration from about 34, 35, 36, 37, 38, or 39 mm to about 40, 41, 42, 43, 44, 45, or 46 mm. In various embodiments, the core 12 can also be made of different materials and/or materials exhibiting different performance characteristics, such as, for example, hardness. In various embodiments, the core 12 can be constructed of a material or materials which can exhibit a Shore A hardness of 30-80. In various embodiments, core 12 can be manufactured to exhibit Shore A hardness, including, but not limited to, 40, 50, or 70. And additional performance characteristic of the material selected for the core 12 can be the elasticity of the material and the elastic recovery of the material.

In various embodiments, the core 12 can be constructed from two components which interact with each other to form the core 12. Each component can have at least two anchoring arms 26, at least two supporting arms 28, and an intermediate region positioned between and separating the anchoring arms 26 from the supporting arms 28. Each intermediate region of each component of a core 12 can have a groove which can have an opening allowing for access to the groove. The groove within an intermediate region of each component of a core 12 provides a location within which a portion of the intermediate region of the other component of the core 12 fits. Once the two components of the core 12 have been joined together, the intermediate region of each of the components forms the node 22 of the core 12. The width dimension of the opening of the groove within each component of the core 12 is smaller than the thickness of the portion of the intermediate region of the component of the core 12 fitted within the groove. An opening of a groove having a width dimension smaller than a thickness of the portion of the component of a core 12 fitted within the groove can result in an interference fit between the two components of the core 12 wherein the two components of the core 12 will remain joined together due to the resultant friction between the two components.

Figure 7A:
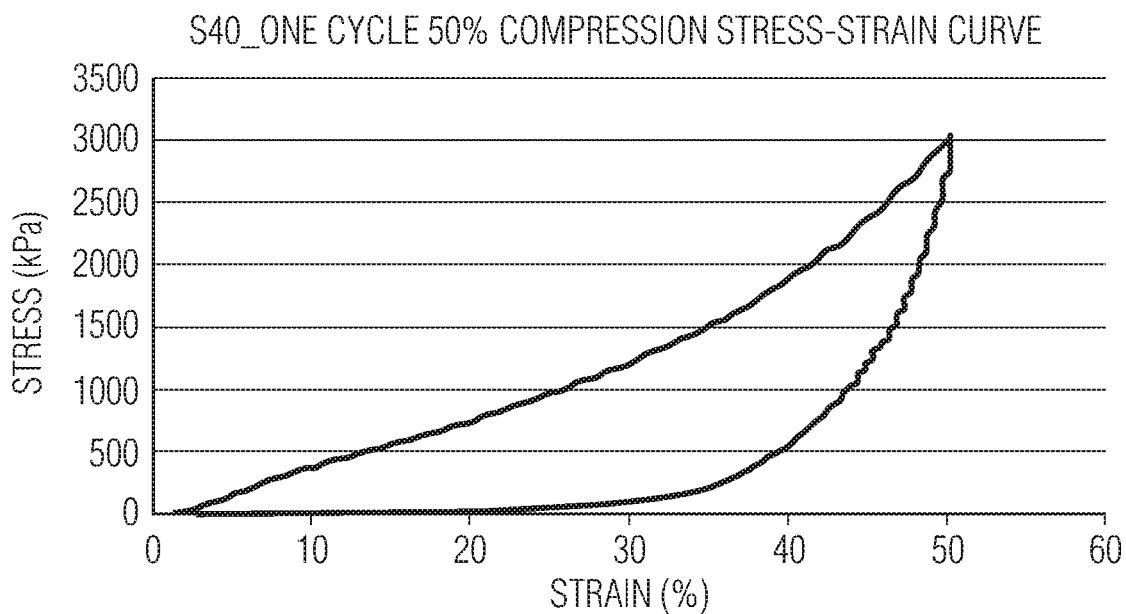
FIG. 7A is an example of a one-cycle compression stress-strain curve of a silicone material having a Shore A hardness of 40.
Figure 7B:
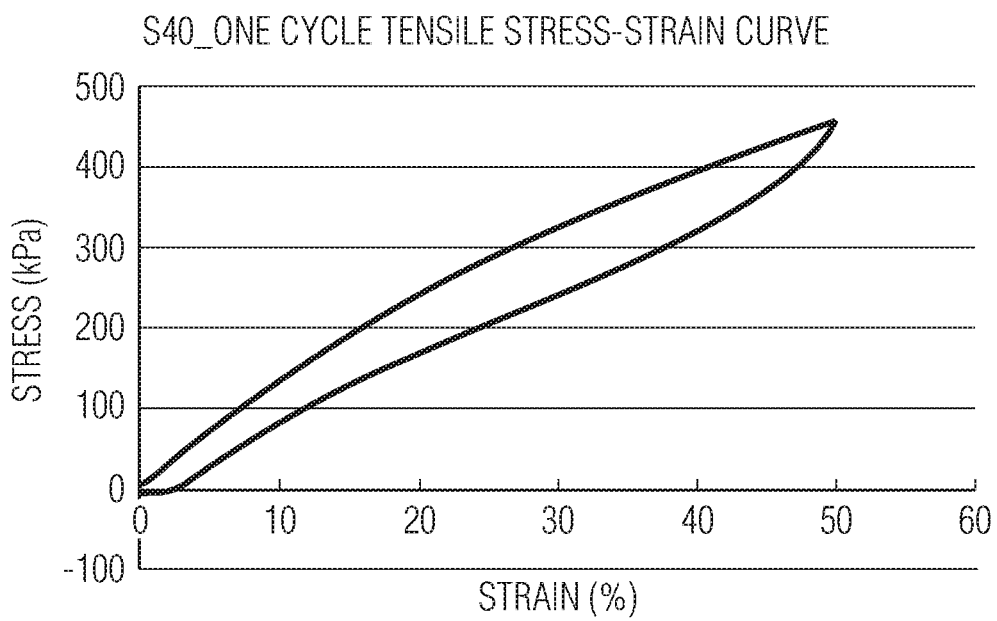
FIG. 7B is an example of a one-cycle tensile stress-strain curve of a silicone material having a Shore A hardness of 40.
Figure 8A:
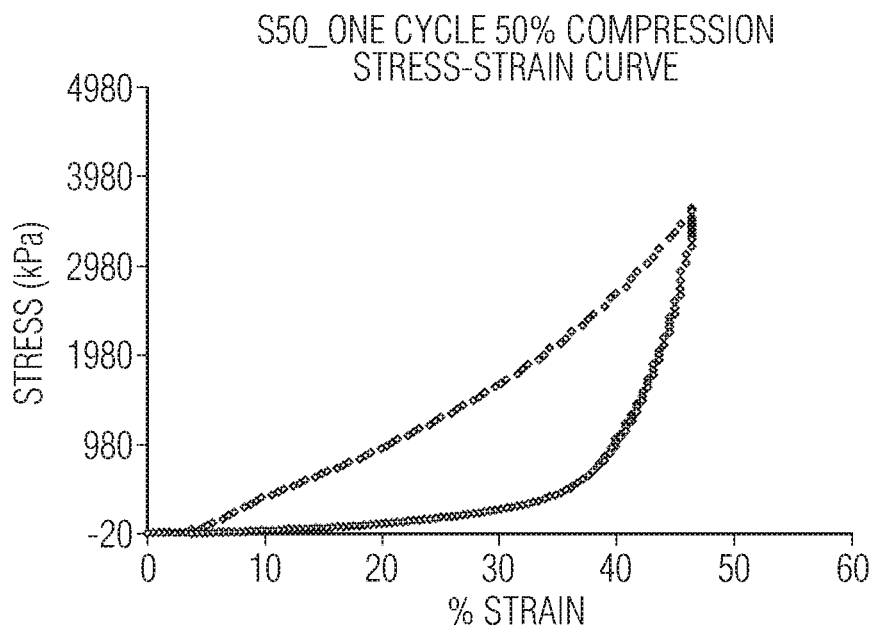
FIG. 8A is an example of a one-cycle compression stress-strain curve of a silicone material having a Shore A hardness of 50.
Figure 8B:
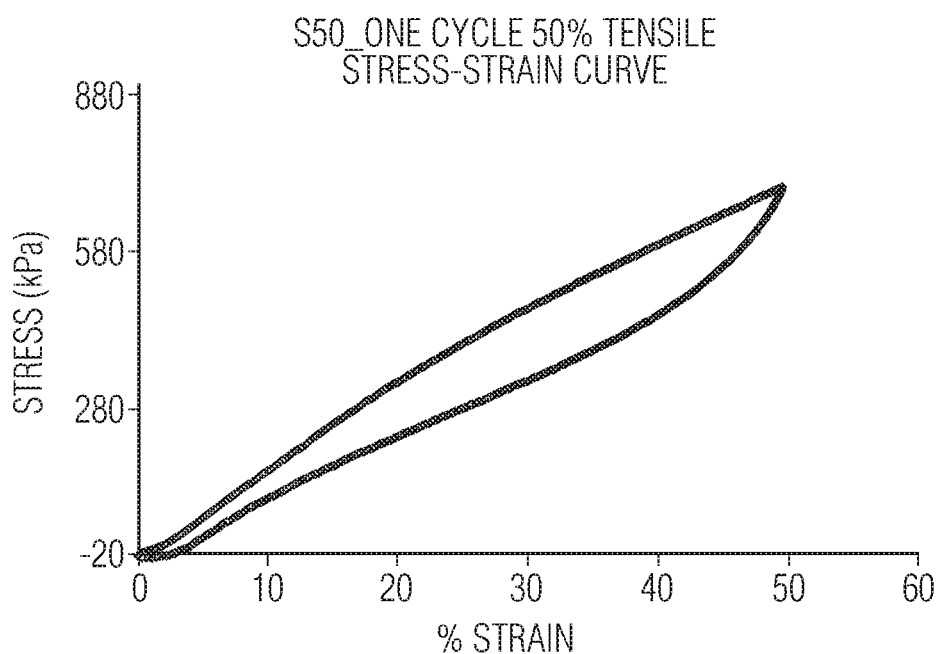
FIG. 8B is an example of a one-cycle tensile stress-strain curve of a silicone material having a Shore A hardness of 50.
Figure 9A:
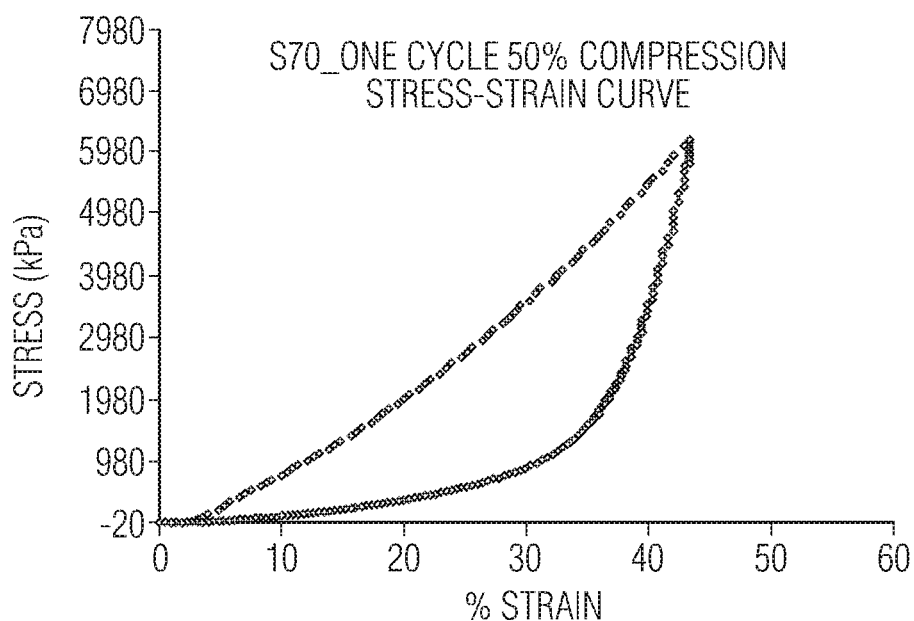
FIG. 9A is an example of a one-cycle compression stress-strain curve of a silicone material having a Shore A hardness of 70.
Figure 9B:
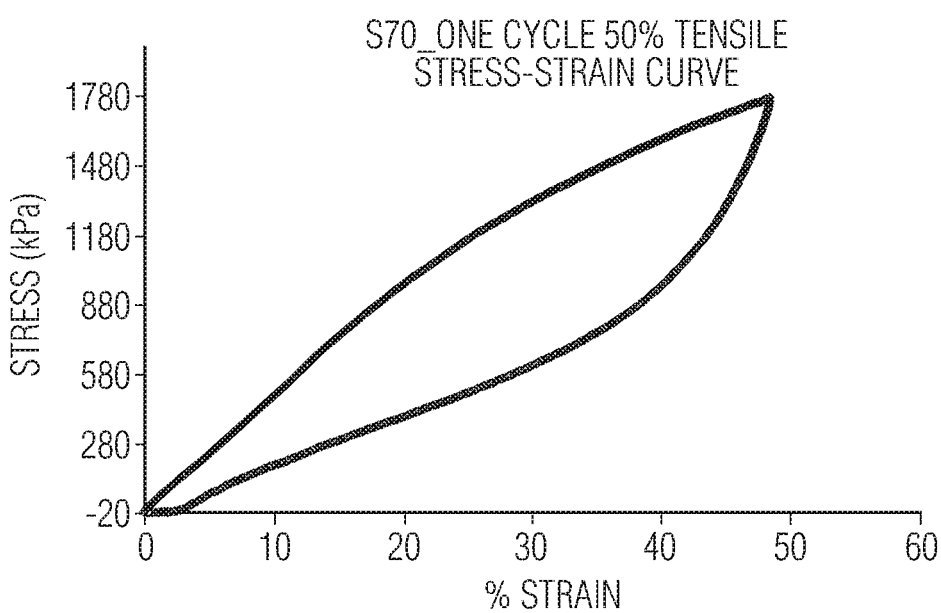
FIG. 9B is an example of a one-cycle tensile stress-strain curve of a silicone material having a Shore A hardness of 70.

In various embodiments, each of the components of a core 12 can be manufactured independently of each other via any manufacturing method deemed suitable. In various embodiments, each of the components of the core 12 can be formed via injection molding such as, for example, each component of the core 12 can be constructed of liquid silicone (LSR) which has been injection molded into the desired component shape. In various embodiments, each of the components of the core 12 can be formed via cutting, such as, for example, die cutting or laser cutting, the desired shape of each component from a chosen construction material. For example, a liquid silicone can be extruded into a sheet of silicone material from which the component shapes can be cut. Once each of the components of the core 12 have been manufactured, they can be brought together into an interference fit arrangement to form the core 12. It is possible to use other materials, for example thermoplastic elastomers (TPE), non-liquid silicone, and others for a core 12 of the same size. In an embodiment, materials exhibiting various degrees of Shore A hardness can be used to produce softer or more rigid cores 12. The degree of rigidity of the components of the core 12 can impact the ability of the dimension of the opening of each groove of each component to increase in order to allow a portion of the intermediate region of a component of the core 12 to fit within a groove of the opposite component of the core 12. In an embodiment, materials exhibiting various degrees of elasticity and elastic recovery can be used to produce components of the core 12. The degree of elasticity and elastic recovery of the components of the core 12 can impact the normal force of each component of the core 12 exerted on the opposite component of the core 12 as the component attempts to return to its original configuration prior to the insertion of a portion of the intermediate region of the opposite component into its groove. To form a core 12 having an interference fit between the two components of the core 12, a material for each component of the core 12 can be selected to have the desired Shore A hardness as well as the desired elasticity and elastic recovery. FIGS. 7A and 7B provide an example of the one-cycle compression stress-strain curves and one-cycle tensile stress-strain curves of a sample of a silicone material having a Shore A hardness of 40. FIGS. 8A and 8B provide an example of the one-cycle compression stress-strain curves and one-cycle tensile stress-strain curves of a sample of a silicone material having a Shore A hardness of 50. FIGS. 9A and 9B provide an example of the one-cycle compression stress-strain curves and one-cycle tensile stress-strain curves of a sample of a silicone material having a Shore A hardness of 70. In various embodiments, the material selected for each component of the core 12 can be the same. In various embodiments, the material selected for each component of the core 12 can be different.

Figure 10A:
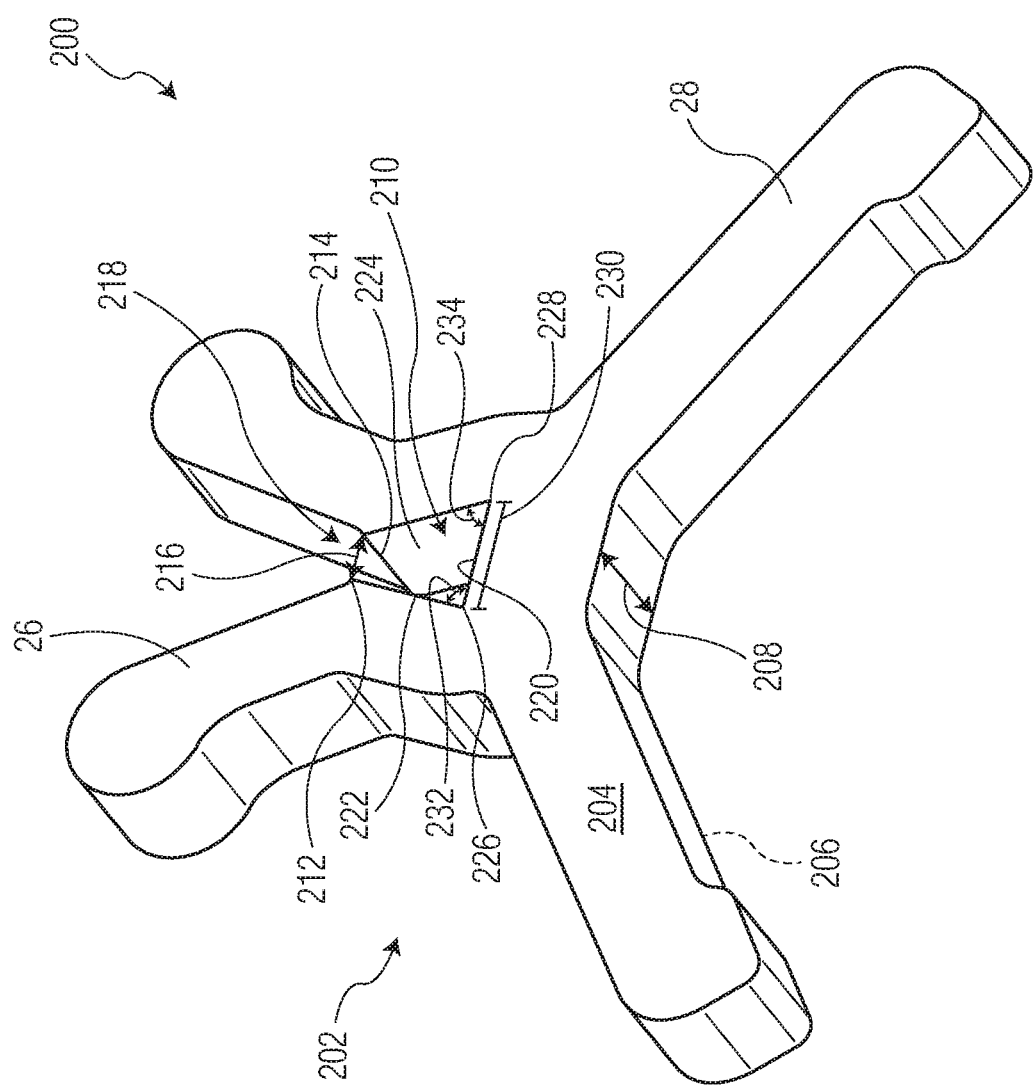
FIGS. 10A and 10B are exemplary embodiments of components of an exemplary embodiment of a core.
Figure 10B:
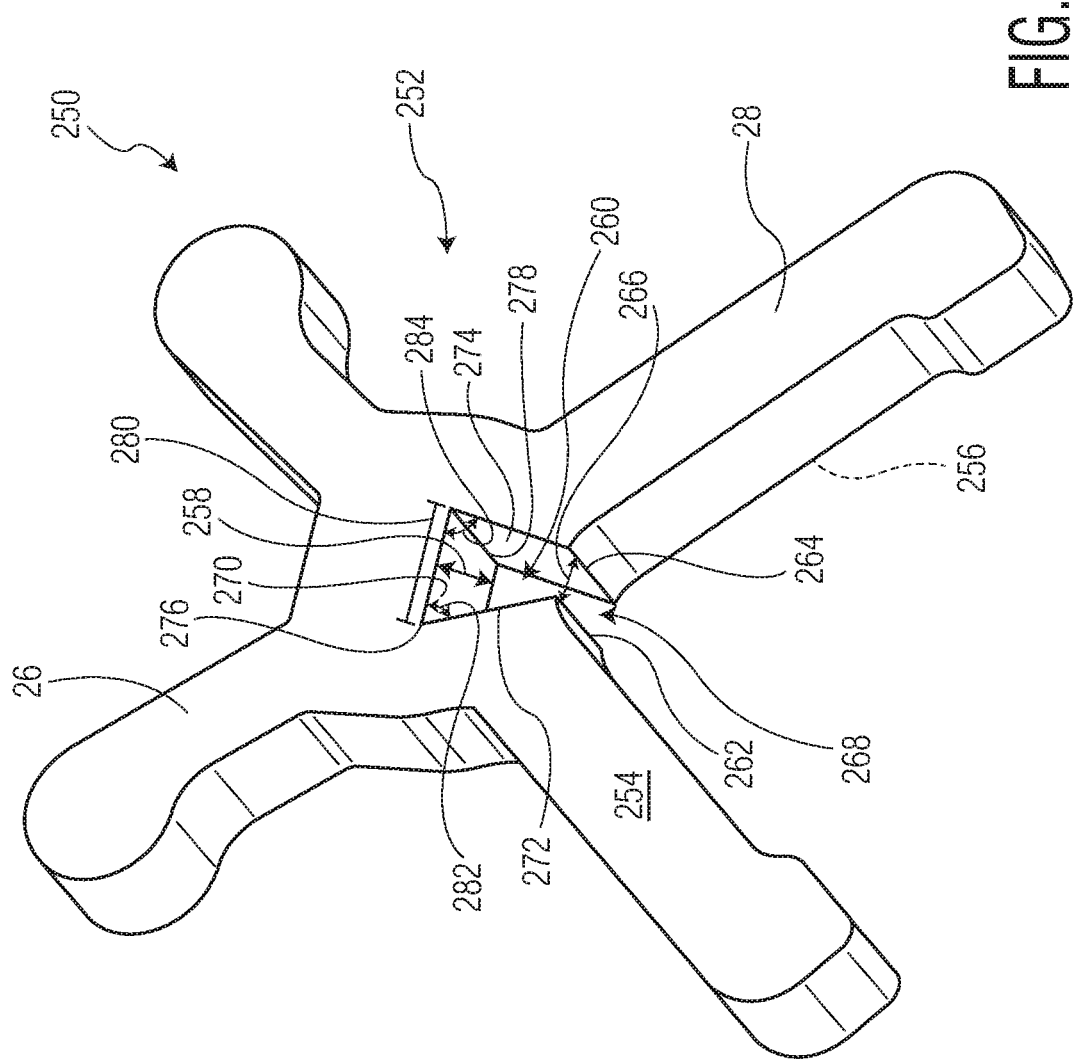

FIGS. 10A and 10B provide exemplary illustrations of an embodiment of two components, 200 and 250, respectively, which can be brought together to form the core 12 illustrated in FIG. 10C. The components, 200 and 250, can be formed via any manufacturing method deemed suitable, such as, for example, injection molding the component shape or cutting the component shape out of the chosen construction material. FIG. 10A provides an exemplary illustration of a first component 200 which has two anchoring arms 26, two supporting arms 28, and an intermediate region 202 positioned between and separating the anchoring arms 26 from the supporting arms 28. The first component 200 can have a first major surface 204 and a second major surface 206 which is spaced apart from the first major surface 204 by a thickness 208. A portion of the intermediate region 202 of the first component 200 can contain a groove 210 which will ultimately receive a portion of the intermediate region 252 of the second component 250 illustrated in FIG. 10B in order to form the core 12 illustrated in FIG. 10C. The groove 210 of first component 200 can extend between and connect the two anchoring arms 26 and can extend from the first major surface 204 to the second major surface 206. As the groove 210 can extend between and connect the two anchoring arms 26, the groove 210 can have a junction between the groove and each of the anchoring arms and can transition to the first anchor arm 26 at a first edge 212 and can transition to the second anchor arm 26 at a second edge 214. The first edge 212 and the second edge 214 can be positioned in a facing relationship to each other and can be spaced apart from each other by a distance 216 wherein the distance 216 defines the width dimension of the opening 218 of the groove 210. The opening 218 of the groove 210 can allow access to the groove 210 for the fitting of a portion of the intermediate region 252 of the second component 250 within the groove 210 of the first component 200 in the formation of the core 12.

The groove 210 of the first component 200 can be bounded by a base wall 220, a first side wall 222, a second side wall 224, and the opening 218. The base wall 220 is joined to the first side wall 222 at a third edge 226 and the base wall 220 is joined to the second side wall 224 at a fourth edge 228. The third edge 226 and the second edge 228 can be spaced apart from each other by a distance 230 wherein the distance 230 defines the width dimension of the base wall 220. The width dimension of the base wall 220 (the distance 230 between the third edge 226 and the fourth edge 228) of the groove 210 of the first component 200 is greater than the width dimension of the opening 218 (the distance 216 between the first edge 212 and the second edge 214) of the groove 210 of the first component 200. For the width dimension of the base wall 220 to be greater than the width dimension of the opening 218, a first angle 232 of less than 90 degrees can be present between the first side wall 222 and the base wall 220 and a second angle 234 of less than 90 degrees can be present between the second side wall 224 and the base wall 220. The groove 210 of the first component 200 can have a trapezoidal shape when the first component 200 is separate from and not combined with the second component 250 to form a core 12.

FIG. 10B provides an exemplary illustration of a second component 250 which has two anchoring arms 26, two supporting arms 28, and an intermediate region 252 positioned between and separating the anchoring arms 26 from the supporting arms 28. The second component 250 can have a first major surface 254 and a second major surface 256 which is spaced apart from the first major surface 254 by a thickness 258. A portion of the intermediate region 252 of the second component 250 can contain a groove 260 which will ultimately receive a portion of the intermediate region 202 of the first component 200 illustrated in FIG. 10A in order to form the core 12 illustrated in FIG. 10C. The groove 260 of second component 250 can extend between and connect the two supporting arms 28 and can extend from the first major surface 254 to the second major surface 256. As the groove 260 can extend between and connect the two supporting arms 28, the groove 260 can have a junction between the groove and each of the supporting arms and can transition to the first supporting arm 28 at a first edge 262 and can transition to the second supporting arm 28 at a second edge 264. The first edge 262 and the second edge 264 can be positioned in a facing relationship to each other and can be spaced apart from each other by a distance 266 wherein the distance 266 defines the width dimension of the opening 268 of the groove 260. The opening 268 of the groove 260 can allow access to the groove 260 for the fitting of a portion of the intermediate region 202 of the first component 200 within the groove 260 of the second component 250 in the formation of the core 12.

The groove 260 of the second component 250 can be bounded by a base wall 270, a first side wall 272, a second side wall 274, and the opening 268. The base wall 270 is joined to the first side wall 272 at a third edge 276 and the base wall 270 is joined to the second side wall 274 at a fourth edge 278. The third edge 276 and the second edge 278 can be spaced apart from each other by a distance 280 wherein the distance 280 defines the width dimension of the base wall 270. The width dimension of the base wall 270 (the distance 280 between the third edge 276 and the fourth edge 278) of the groove 260 of the second component 250 is greater than the width dimension of the opening 268 (the distance 266 between the first edge 262 and the second edge 264) of the groove 260 of the second component 250. For the width dimension of the base wall 270 to be greater than the width dimension of the opening 268, a first angle 282 of less than 90 degrees can be present between the first side wall 272 and the base wall 270 and a second angle 284 of less than 90 degrees can be present between the second side wall 274 and the base wall 270. The groove 260 of the second component 250 can have a trapezoidal shape when the second component 250 is separate from and not combined with the first component 200 to form a core 12.

To form the core 12, the first component 200 and the second component 252 can be brought together so that a portion of the intermediate region 202 of the first component 200 fits within the groove 260 of the second component 250 and a portion of the intermediate region 252 of the second component 250 fits within the groove 210 of the first component 200. When the first component 200 and the second component 250 are brought together, the first side wall 222 and the second side wall 224 bounding the groove 210 of the first component 200 are contacting the first major surface 254 and the second major surface 256 of the intermediate region 252 of the second component 250, respectively, and the first side wall 272 and the second side wall 274 bounding the groove 260 of the second component 250 are contacting the first major surface 204 and the second major surface 206 of the intermediate region 202 of the first component 200, respectively. The total amount of contact area between each of the side walls, 222, 224, 272, and 274, and the major surfaces, 204, 206, 254, and 256, is the total sum of the areas of each of the side walls, 222, 224, 272, and 274. As described herein, the width dimension of the opening of the groove within each component of the core 12 is smaller than the thickness of the portion of the intermediate region of the component of the core 12 fitted within the groove. The opening 218 of the groove 210 of the first component 200 has a width dimension (the distance 216 between the first edge 212 and the second edge 214 of the groove 210 of the first component 200) which is smaller than the thickness 258 of the portion of the intermediate region 252 of the second component 250 that is to be fitted within the groove 210 of the first component 200. The opening 268 of the groove 260 of the second component 250 has a width dimension (the distance 266 between the first edge 262 and the second edge 264 of the groove 260 of the second component 250) which is smaller than the thickness 208 of the portion of the intermediate region 202 of the first component 200 that is to be fitted within the groove 260 of the second component 250. During the assembly of the core 12 by bringing the first component 200 and the second component together the thickness of the portion of the intermediate region 202 of the first component 200 fitting within the grove 260 of the second component 250 will push the first edge 262 and the second edge 264 of the groove 260 of the second component 250 away from each other increasing the distance 266 between the first edge 262 and the second edge 264 of the groove 260 of the second component 250 and the thickness of the portion of the intermediate region 252 of the second component 250 fitting within the groove 210 of the first component 200 will push the first edge 212 and the second edge 214 of the groove 210 of the first component 200 away from each other increasing the distance 216 between the first edge 212 and the second edge 214 of the groove 210 of the first component 200. Increasing each of the distances, 216 and 266, of the width dimensions of the openings, 218 and 268, respectively, of the grooves, 210 and 260, respectively, as a result of the larger thicknesses of each of the portions of the intermediate regions, 202 and 252, can result in a an interference between the two components, 200 and 250, and a contact normal force being exerted on each of the portions of the intermediate regions, 202 and 252, being fitted within each of the grooves, 210 and 260, by each of the side walls, 222, 224, 272, and 274, respectively. The degree of the exerted contact normal force exerted by each side wall, 222, 224, 272, and 274, is the product of the normal stress of the material selected for the component, 200 or 250, respectively, and the contact area of each side wall, 222, 224, 272, and 274. The material selected for each component, 200 and 250, of the core 12 can also have a static surface coefficient of friction. When a side wall, such as side wall 222 of the first component 200, is in contact with a surface of a portion of the intermediate region of the opposite component, such as intermediate region 252 of the second component 250, a static contact coefficient of friction can exist between those two surfaces being in contact with each other. The product of the contact normal force and the static contact coefficient of friction is a contact frictional force between the two components, 200 and 250, of the core 12. In order to maintain an interference fit between the two components, 200 and 250, the contact frictional force between the two components, 200 and 250, is greater than a separation force that may be applied to one of the components, 200 or 250. Separation of the two components, 200 and 250, from each other can occur when the contact frictional force between the two components, 200 and 250, is less than a separation force being applied to one of the components, 200 or 250. A contact frictional force deemed suitable to maintain two components, 200 and 250, in an interference fit can be arrived at through the selection of a material for each component of the core 12 having the desired one-cycle compression stress-strain curve, one-cycle tensile stress-strain curve, Shore A hardness, and static coefficient of friction. The greater the Shore A hardness and the higher the elasticity and elastic recovery of the material utilized for the first component 200 and second component 250, then a smaller difference between the width dimension of the opening of a groove and the thickness of the intermediate region fitted within the groove will be sufficient to maintain the first component 200 and the second component 250 in an interference fit arrangement. The lower the Shore A hardness and the lower elasticity and elastic recovery of the material utilized for the first component 200 and second component 250, then a larger difference between the width dimension of the opening of a groove and the thickness of the intermediate region fitted within the groove will be needed to maintain the first component 200 and the second component 250 in an interference fit arrangement. In various embodiments, the width dimension of an opening of a groove can be from about 10, 15, 20, 25, 30, 35, 40, 45, or 50% to about 55, 60, 70, 75, 80, 85, or 90% of the thickness of the intermediate region to be fitted within the groove.

As will be described herein, a core 12 can have a migration reduction feature 70 (such as described in the description of FIGS. 18A-18D) and/or a migration reduction feature 100 (such as described in the description of FIGS. 19A-19E). In various embodiments, the core 12 (such as illustrated in the exemplary embodiments of FIGS. 10A-10C) can have a migration reduction feature 70. It is to be noted that such a migration reduction feature 70 is optional. In various embodiments, the core 12 (such as illustrated in the exemplary embodiments of FIGS. 10A-10C) can have a migration reduction feature 100. It is to be noted that such a migration reduction feature 100 is optional. In various embodiments, the core 12 (such as illustrated in the exemplary embodiments of FIGS. 10A-10C) can have a migration reduction feature 70 and a migration reduction feature 100 and such migration reduction features, 70 and 100, are optional.

Referring to FIG. 1, a perspective view of a core 12 enclosed within a cover 14 provided with a removal element 16 is illustrated, in accordance with an exemplary embodiment of the vaginal insert 10. Cover 14 can be optionally any of the covers described in PCT/IL2004/000433; PCT/IL2005/000304; PCT/IL2005/000303; PCT/IL2006/000346; PCT/IL2007/000893; PCT/IL2008/001292; U.S. Provisional Patent Application No. 60/719,422; U.S. Provisional Patent Application No. 60/762,059; and U.S. Provisional Patent Application No. 60/960,492.

In various embodiments, the cover 14 can be smooth. In various embodiments, the cover 14 can be formed from woven or non-woven material. Woven materials can include, but is not limited to, textile fabrics which can be made from rayon, cotton, polyolefins, or other synthetic yards. The synthetics can be either staple or continuous filaments. Non-woven materials can include, but are not limited to, spunbond, bonded carded webs, and hydroentangled webs. In various embodiments, the cover 14 can be constructed from a spunbond non-woven material. In various embodiments, the cover 14 can be treated with an aqueous solution to reduce frictional drag and to enhance the ease of insertion into and withdrawal from a woman's vagina. In various embodiments, the cover 14 can be constructed of a non-woven material such as a 33 gsm non-woven Fiberweb®, Catalog No. 097YLJO09P. In various embodiments, the cover 14 can be constructed of a non-woven material, such as, for example, constructed of about 50% polypropylene and about 50% polyethylene. In various embodiments, the cover 14 can be constructed of nylon. In various embodiments, the cover 14 and the removal element 16 can be constructed of the same unitary piece of material and/or at the same time and/or in the same process. In various embodiments, the cover 14 and the removal element 16 can be constructed of separate pieces of material. In various embodiments, the cover 14 can be constructed of a non-absorbent material. In various embodiments, the cover 14 can be flexible and/or stretchable. In various embodiments, the cover 14 can be formed from a heat-shrinkable material. In various embodiments, the cover 14 can be formed from a material which can be extensible and/or elastic. In various embodiments, elements of the cover 14 can be bonded, stitched, sutured, and/or welded together. In various embodiments, the bonds, stitches, sutures, and/or welds can be located inside the cover 14 opposite the vaginal wall. In various embodiments, the cover 14 and/or the core 12 can be adapted to allow the free flow of vaginal discharge.

In various embodiments, the removal element 16 can be constructed of a cotton material but can be constructed of other materials. In various embodiments, the removal element 16 can be constructed of materials which can allow for absorbing fluids or can be constructed of materials which do not allow for absorbing fluids. In various embodiments, the removal element 16 can be a thread or ribbon made from 100% cotton fibers. In various embodiments, the removal element 16 can be constructed of non-absorbent polyurethane, optionally with a coating of silicone film which can provide a smooth surface to the removal element 16. In various embodiments, the removal element 16 can be a silicone coated, braided polyester, an example of which is manufactured by Ashaway.

In various embodiments, the removal element 16 of the vaginal insert 10 can be from about 14 cm to about 16 cm in length, although the length can be varied in different vaginal insert 10 configurations. In an embodiment, the removal element 16 can be secured to the cover 14 in a position whereby a pulling force towards the vaginal introitus can be substantially evenly distributed over the cover 14 as it collapses the supporting arms 28 of the core 12 within the vagina. In an embodiment, this position can be in the center of the cover 14 in the supporting element 20 region, such as illustrated in FIG. 1.

In various embodiments, the cover 14 can reduce friction between the vaginal insert 10 and the vaginal wall. Pulling the removal element 16 can cause tensioning of the cover 14. Tensioning of the cover 14 can result in the straightening of the vaginal walls which can thereby reduce the tent-like effect described above and relieve tension applied to the vaginal insert 10, allowing for an easy and smooth removal of the vaginal insert 10 from the vagina. Furthermore, pulling on the removal element 16 can cause the collapse of supporting arms 28 at least slightly towards the longitudinal axis 24 as a result of the force applied to them by cover 14, thereby reducing the radial diameter of the core 12 and allowing for an easy and smooth removal of the vaginal insert 10 from the vagina.

Besides being used as an aide in removal of the vaginal insert 10, an additional use of the cover 14 can be to act as a sling stretched between supporting arms 28, which can supply sub-urethral tension-free support to the urethra.

Figure 11:
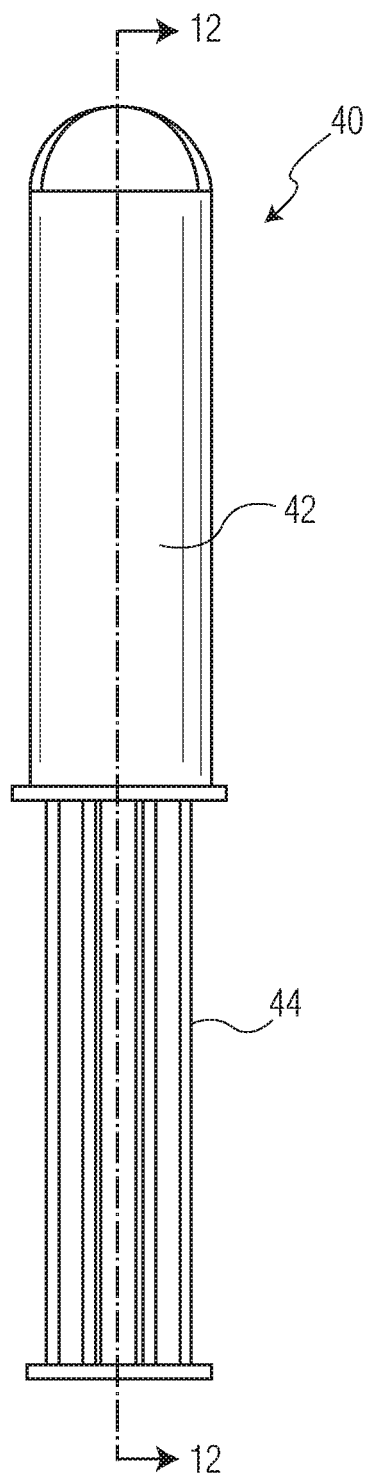
FIG. 11 is a perspective view of an exemplary embodiment of an applicator for a vaginal insert.
Figure 12:
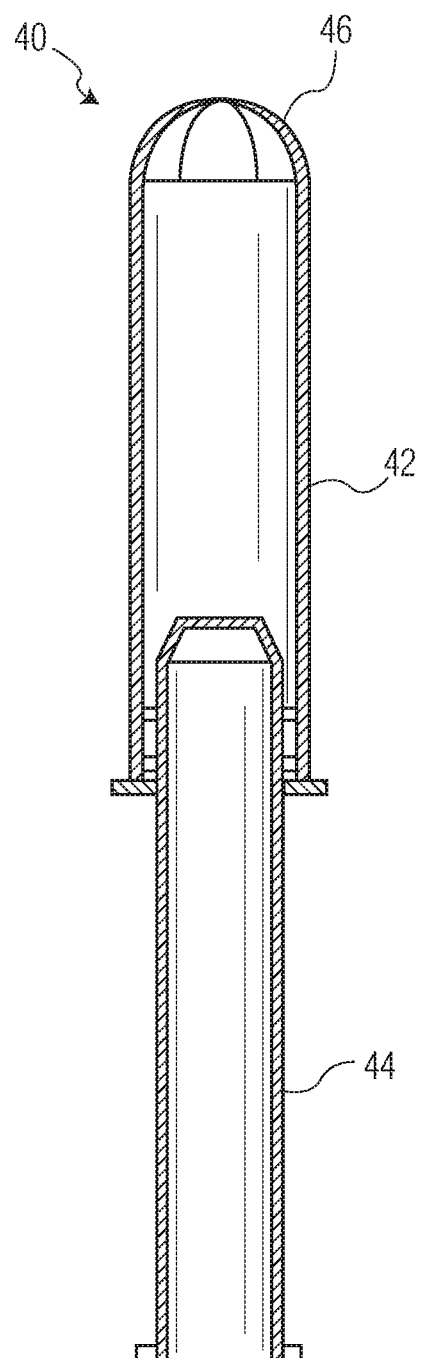
FIG. 12 is a cross-sectional view of the applicator of FIG. 11 taken along line 12-12.
Figure 13:
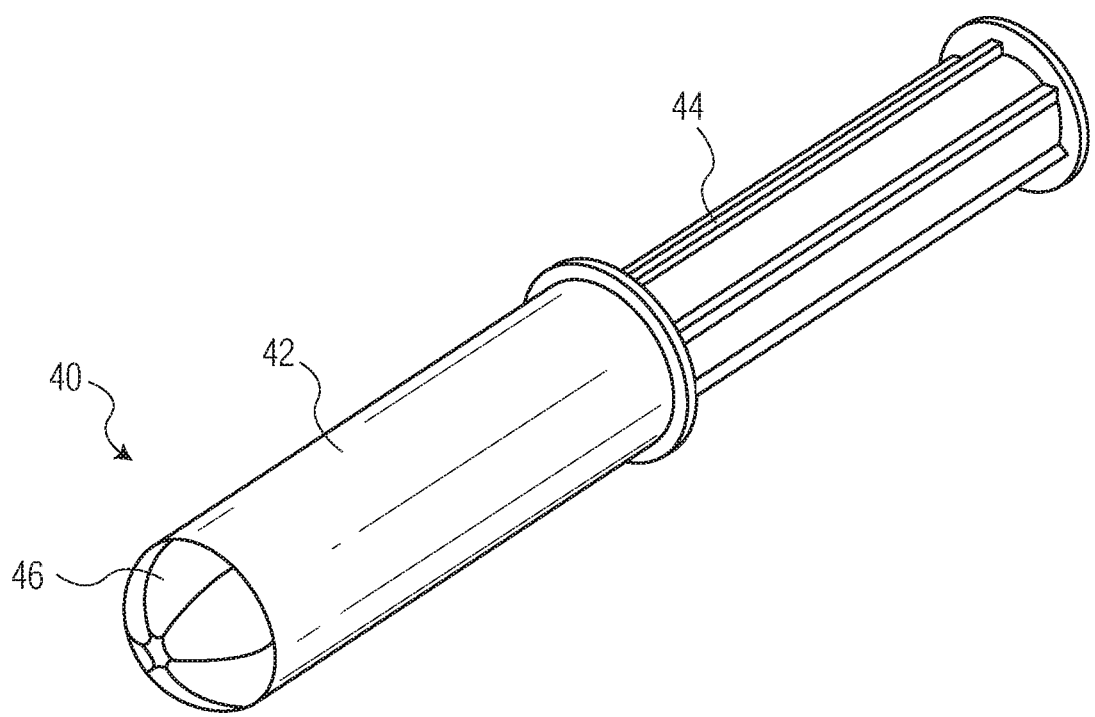
FIG. 13 is a perspective view of the applicator of FIG. 11.

Referring to FIGS. 11-13, views of an applicator 40 which can be utilized to deploy a vaginal insert 10 for treating urinary incontinence are illustrated. In an embodiment, the applicator 40 can comprise a housing 42 and a plunger 44. The housing 42 can be adapted for receipt and/or storage of the vaginal insert 10. In various exemplary embodiments, plunger 44 can be used to expel the vaginal insert 10 from the housing 42 during vaginal insert 10 deployment into a vagina. FIG. 12 is a cross-section of the applicator 40 of FIG. 11 along line 12-12 which can show the configuration of applicator 40 more clearly, including the interface between housing 42 and plunger 44. In various embodiments, housing 42 can be provided with an outlet 46. In various embodiments, outlet 46 can be provided with a plurality of flexible flaps ("petals") which can be pushed open when vaginal insert 10 is expelled from applicator 40. The outlet 46 is more clearly shown in FIG. 13.

In the applicator 40, the vaginal insert 10 can be positioned such that the anchoring element 18 of the core 12 comes out of the applicator 40 into the vagina first, followed by supporting element 20 of the core 12, which comes out at the end of the deployment process. In an embodiment, the vaginal insert 10 can be deployed to render support to the urethra. In an embodiment, the vaginal insert 10 can be deployed to render support to the bladder neck.

Figure 14:
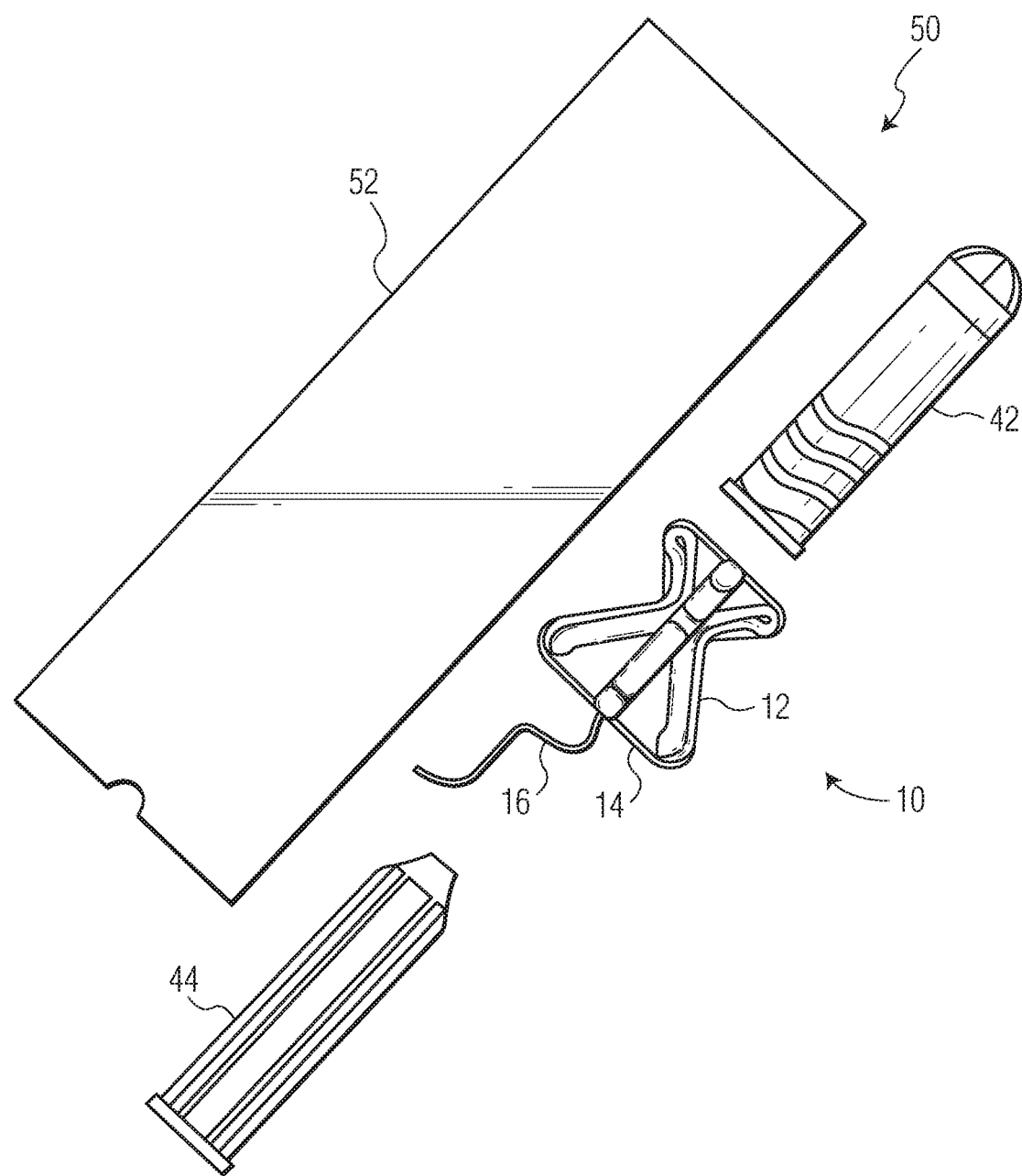
FIG. 14 is a side view of an exemplary embodiment of the component parts of a product package for a vaginal insert.

In an embodiment, a user can receive the vaginal insert 10 in an individual package 50 such as shown in FIG. 14. In an embodiment, different sizes and/or packages 50 with vaginal inserts 10 having different features can be color coded for ease of identification by a user of the vaginal insert 10. FIG. 14 is a side view of the component parts of a product package 50 for a vaginal insert 10 for treating urinary incontinence. Product package 50 can comprise an applicator housing 42, core 12, cover 14, removal element 16, applicator plunger 44, and product wrapper 52. In an embodiment, product wrapper 52 can be wrapped around the applicator 40, which when packaged can include the vaginal insert 10 within the housing 42. Thus, the product package 50 in its assembled form can be more or less cylindrical or shaped like a wrapped tampon.

In an embodiment, insertion of the vaginal insert 10 into the vagina can be similar to insertion of a tampon. The user can use one hand to spread the labia, direct the anterior part of the applicator 40 into the vagina, and compress the plunger 44 with the other hand, thereby deploying the vaginal insert 10 from the applicator 40 into the vagina. In an embodiment, there is no specific need for a specific orientation of the vaginal insert 10 because of the generally symmetrical design of the core 12 about the longitudinal axis 24 of the core 12. The insertion of the vaginal insert 10 can be performed at any orientation and/or anywhere in the 360° around the longitudinal axis 24 of the core 12 in the applicator 40.

In various embodiments, even though the core 12 can be designed symmetrically, because each of the arms, 26 and 28, can flex independently of the other arms, 26 and 28, when in situ and each vagina varies in shape slightly, the vaginal insert 10 may not actually be in symmetrical form when in use (see FIG. 5). Referring to FIG. 5, a plan view showing a possible relationship of the supporting arms 28 to the longitudinal axis 24 of the core 12 when the vaginal insert 10 is in situ is illustrated. It is noted that not every vagina has the same contours and internal structure, even though some generalizations can be made about vaginal anatomical features. To that end, the core 12 can be designed to be adaptable to the varying vaginal features it may come across, depending on the user of the vaginal insert 10. For example, each of the supporting arms 28 of the core 12 can be capable of functioning independently. This can enable maximal flexibility, maximal adjustment to any vaginal shape (cross section) and/or vaginal dimensions. Thus, it may happen that in a given cross section, the supporting arms 28 of the core 12 will not be symmetrically spread around the longitudinal axis 24 of the core 12, such as shown in FIG. 5.

The core 12, formed from two components, 200 and 250, can be manufactured and/or commercially available in a plurality of sizes, with each size exhibiting different performance characteristics, operational dimensions, weight, and the like. In various embodiments, differently sized cores 12 can be made of the same material. In various embodiments, differently sized cores 12 can use different materials and/or different material ratios. FIGS. 15A-15C, are a series of charts Illustrating exemplary core 12 sizes. As can be seen in the charts of FIGS. 15A-15C, core 12 can be produced in at least four sizes for optimal adjustment to various vaginal dimensions and/or in accordance with the severity of urinary incontinence. The various sizes can differ in the diameter of the supporting arm's 28 spread and as a result, can differ in the overall length when deployed (i.e., the supporting arms 18 are spread). In various embodiments, the anchoring arms 26 can have identical deployed dimensions and/or performance characteristics in all of the sizes.

In various embodiments, core 12 can be constructed of liquid silicone (LSR) by injection molding. It is possible to use other materials, for example thermoplastic elastomers (TPE), non-liquid silicone, and others for a core 12 of the same size. In an embodiment, materials exhibiting various degrees of Shore A hardness can be used to produce softer or more rigid cores 12.

It should be understood that the various size combinations can be made by varying the size and/or Shore A hardness. For example, sizes 1 and 2, could be made with a Shore A hardness of 70 while sizes 3 and 4 can have a Shore A hardness of 40. In various embodiments, all of the core 12 sizes can exhibit the same Shore A hardness. In various embodiments, each individual size can be made in multiple versions, each exhibiting a different Shore A hardness. In sum, various combinations and permutations of features, sizes, performance characteristics and/or construction materials can be employed to apply desired sub-urethral supporting force at certain working angles.

In various embodiments, the radiating supporting arms 28 of core 12 can create an overall core 12 diameter from about 34 or 41 mm to about 50, 51 or 52 mm at the widest supporting element 20 cross section within the vaginal cavity. In various embodiments, the diameter can be larger or smaller depending on the individual needs of the user.

FIG. 16 is a core 12 performance graph correlating expansive force exerted by supporting arms 28 (y-axis) to amount of medial deflection (x-axis) and hardness (line hatchings) for each of the four basic sizes shown in FIGS. 15A-15C whereby medial deflection is the distance in mm towards the longitudinal axis 24 of the core 12 from the natural expanded state of the supporting arm 28.

The expansive force exerted by the supporting arms 28 is generally determined by the hardness grade and/or the medial flexion degree (medial deflection) of each of the supporting arms 28 relative to the longitudinal axis 24. If a specific material is used in construction of the core 12, such as, for example, liquid silicone, these forces can be measured for any given diameter of the supporting arms 28 of the core 12, knowing the performance characteristics of the specific material being used. Using this data in a graph where the x-axis represents the core 12 diameter and the y-axis represents the force, the forces exerted by the supporting arms 28 for a given core 12 size and its material hardness grade can be demonstrated. The slope represents the ratio between the force (grams) and the amount of medial deflection (mm).

In designing and/or selecting a core 12 for use, certain performance considerations can be taken into account. It should be noted that core 12 support is "activated" by the supporting arms 28 being compressed (i.e., deflected towards the longitudinal axis 24 of the core 12, or "medial deflection") at least slightly by the vaginal wall. In general, the stronger the compressive forces on the supporting arms 28, the stronger the support force that is exerted back onto the vaginal wall/sub-urethra by the supporting arms 28. For example, supporting arms 28 must be compressed a certain minimal amount in order to provide counterforce sufficient for the supporting arms 28 to render support. That is, if a vaginal insert 10 is inserted into a vagina and the core 12 is too small or the angle of radial expansion is too small, then not enough force will be applied to the supporting arms 28 from the vaginal wall to cause the supporting arms 28 to counter with the force required to render appropriate and effective support. Failure to achieve this minimal value of compression in an at-rest state, shown as a horizontal minimal applied force line 60 in FIG. 16 at approximately 10 g of force, on the supporting arms 28 during a stressful event will reduce vaginal insert 10 efficacy. It should be noted that in some embodiments, the minimal applied force line 60 at 10 g is approximate and can vary ±3 grams.

Similarly, there exists a maximum force exerted by the core 12 on the vaginal walls beyond which the user would experience discomfort while the vaginal insert 10 is in the vagina at-rest and/or while removing the vaginal insert 10. In an embodiment, therefore, the core 12 can be designed and/or selected for use not to exceed this maximal force. This maximal force is represented in FIG. 16 as the bold horizontal line 62 at approximately 50 g of force. In an embodiment, 50 grams is approximate and can vary ±5 grams. For example, if the radial expansion of the supporting arms 28 is too great, it will generate excessive force on the vaginal wall and the user may experience discomfort, which is to be avoided.

The graph of FIG. 16 can be used, in various embodiments, to determine the use potential for a specific core 12 configuration for a specific vaginal size. For example, D1 on the graph represents a vagina with a diameter of 33 mm. Referring to FIG. 16, it can be seen that size 1 cores 12 with Shore A hardnesses of S40 and S50 are not indicated for use with this user because they will not provide sufficiently effective support in an at-rest state. However, a number of other core 12 sizes and Shore A hardnesses are considered acceptable:

Size 1 with Shore A hardness of 70 device (supplying force of about 21 grams)
Size 2 with Shore A hardness of 50 device (supplying force of about 25 grams)
Size 2 with Shore A hardness of 40 device (supplying force of about 20 grams)
Size 3 with Shore A hardness of 50 device (supplying force of about 38 grams)
Size 3 with Shore A hardness of 40 device (supplying force of about 28 grams)
Size 4 with Shore A hardness of 50 device (supplying force of about 48 grams)
Size 4 with Shore A hardness of 40 device (supplying force of about 35 grams)

As another example, D2 on the graph represents a vagina with a diameter of 42.5 mm. Because of the size of this user's vagina, fewer choices may be available for receiving ideally efficacious vaginal support. In this example, likely choices would include:

Size 3 with Shore A hardness of 70 device (supplying force of about 22 grams)
Size 4 with Shore A hardness of 70 device (supplying force of about 45 grams)
Size 4 with Shore A hardness of 50 device (supplying force of about 22 grams)
Size 4 with Shore A hardness of 40 device (supplying force of about 18 grams)

It is noted that a size 4 core 12 made of a low Shore A hardness material, for example 40, can be used for a wide variety of vaginal diameters (approximately 30 mm to 45 mm), in an exemplary embodiment.

Above the maximum force line 62, the graph of FIG. 16 shows force exertion levels of the various core 12 sizes at different levels of medial deflection all the way down to about 12 mm in total core 12 diameter. In an embodiment, each arm is approximately 6 mm in width, therefore the minimum diameter distance possible is when two opposing arms have come into contact or 12 mm (6 mm+6 mm). Specific numbers for selected core 12 sizes are shown in and described in more detail below with respect to FIG. 17.

FIG. 17 is a table showing specific performance levels for exemplary basic core 12 sizes and Shore A hardnesses depicted in FIG. 16. The minimal diameter column lists the diameter (in mm) at which two opposing arms 28 come into contact thereby substantially prohibiting any further medial deflection by the arms 28. In an embodiment, maximal force is exerted when the cores 12 are compressed the most, or at the minimal diameter. The max force column lists the maximum amount of force exerted by each listed core 12 size and Shore A hardness at the 12 mm diameter level.

It is noted that some of the information shown in FIG. 17 is also included in the tables of FIGS. 15A-15C. Where the information is not entirely in conformance, it should be understood that the broadest range of values is to be attributed to the embodiments described herein. For example, a range of values may be taken where the low end of the range is from one table and the high end of the range is from another table. It should also be noted that values given are by way of example only, and that core 12 performance characteristics can vary depending on materials used for construction and/or core 12 size and/or Shore A hardness.

In various embodiments, many of the possible sizes of cores 12 can be suitable for a particular user and sufficient support can be provided without surpassing the discomfort threshold. This can be particularly true with cores 12 of low Shore A hardness and moderate slope. For example, a core 12 of size 3 (support diameter—45 mm) made of soft silicone with a Shore A hardness of 40 may be suitable for a broad range of vaginal diameters: exerting a force of 12 grams over a diameter of 40 mm, 21 grams over a diameter of 35 mm, and 31 grams over a diameter of 30 mm. In other words, in some embodiments, a single core 12 size can provide support to numerous vaginal dimensions. In an embodiment, a core 12 can be adapted to be usable by a variety of users, for example by designing a core 12 with a low or moderate slope.

It is possible that only one size of core 12 will be suitable for a woman with a certain vaginal diameter, especially if her vaginal dimensions are larger than the average. In some embodiments, only sizes 3 or 4 would be suitable, while the smaller sizes would not exert the minimal support force required. It should be noted that characteristics such as the force applied, the size of the vaginal insert 10 and/or overall comfort of the vaginal insert 10 chosen is highly dependent on each individual user and may also depend on the pathological response caused by the vaginal insert 10 for each individual user.

In an exemplary embodiment, reducing the distance between the supporting tip 32 of a supporting arm 28 and the longitudinal axis 24 of the core 12 would increase the force exerted by the core 12 at the supporting tip 32. The operative significance of this can be that a relatively large vaginal insert 10 inserted into the vagina would exert a higher force on the vaginal walls as compared to a smaller vaginal insert 10 inserted into the same vagina. Using this same rationale, if external forces exerted on the vaginal insert 10 reduce the internal distance between its supporting arms 28 and the longitudinal axis 24 (e.g. during coughing, jumping, sneezing, etc.), a greater counteracting force would be exerted by the supporting arms 28 on the vaginal walls, thus enhancing the urethral support and the efficiency of urinary leak prevention. Therefore, in an exemplary embodiment, a vaginal insert 10 can be designed with this activity-generated counter tension in mind.

As described herein, a core 12 of a vaginal insert 10 can be manufactured in a variety of sizes, with each size different from another size, wherein the difference can be one of exhibiting a different performance characteristic, material hardness, operational dimension, weight, overall diameter of the supporting element 20 of the core 12 when the supporting arms 28 are radially expanded, and/or the radial spread angle at which the supporting arms 28 protrude outwardly relative to the longitudinal axis 24 of the core 12. The variety of cores 12 can, therefore, result in a variety of vaginal inserts 10. A manufacturer of such a variety of vaginal inserts 10 may find it beneficial (such as, related to cost and simplifying the manufacturing process) to place the resultant variety of vaginal inserts 10 into the same size of applicator 40 (such as illustrated in FIGS. 11-13). In other words, in various embodiments, one size of applicator 40 can be used to house any of the variety of vaginal inserts 10 wherein a vaginal insert 10 can have a core 12 which can differ from the core 12 of a second vaginal insert 10.

As a non-limiting example, the following are three examples of different sizes of cores 12 contemplated by the current disclosure which can be utilized in a vaginal insert 10 contemplated by the current disclosure:

A first core 12 can have an anchoring element 18, a supporting element 20, and a node 22 located between the anchoring element 18 and the supporting element 20. In the radially expanded configuration, the anchoring element 18 of the first core 12 can have a diameter of about 32 mm±1 mm, the supporting element 20 can have a diameter of about 41 mm±1 mm, and the longitudinal length of the first core 12 can be about 42 mm±1 mm. The first core 12 can be manufactured from a soft silicone polymer and can have a Shore A hardness of 50.

A second core 12 can have an anchoring element 18, a supporting element 20, and a node 22 located between the anchoring element 18 and the supporting element 20. In the radially expanded configuration, the anchoring element 18 of the second core 12 can have a diameter of about 32 mm±1 mm, the supporting element 20 can have a diameter of about 50 mm±1 mm, and the longitudinal length of the second core 12 can be about 37 mm±1 mm. The second core 12 can be manufactured from a soft silicone polymer and can have a Shore A hardness of 50.

A third core 12 can have an anchoring element 18, a supporting element 20, and a node 22 located between the anchoring element 18 and the supporting element 20. In the radially expanded configuration, the anchoring element 18 of the third core 12 can have a diameter of about 32 mm±1 mm, the supporting element 20 can have a diameter of about 50 mm±1 mm, and the longitudinal length of the third core 12 can be about 37 mm±1 mm. The third core 12 can be manufactured from a soft silicone polymer and can have a Shore A hardness of 70.

In the example just described, the first core 12 and the second core 12 can exhibit the same Shore A hardness of 50 but the third core 12 can exhibit a Shore A hardness which is different from the Shore A hardness of the first core 12 and second core 12. While the first core 12 and the second core 12 can have the same Shore A hardness, the supporting element 20 of each of the first core 12 and the second core 12 can have different diameter dimensions when in the radially expanded configuration. In the example just described, the supporting element 20 of each of the second core 12 and the third core 12 can have the same diameter dimension when in the radially expanded configuration.

Each of the first core 12, second core 12, and third core 12 can be utilized in the manufacture of a vaginal insert 10 as contemplated by this disclosure. As mentioned above, in such a non-limiting example, a manufacturer of such a variety of cores 12, and the resultant variety of vaginal inserts 10, may find it beneficial (such as, related to cost and simplifying the manufacturing process) to insert each of the cores 12 just described, and the resultant variety of vaginal inserts 10, into the same size of applicator 40 (such as illustrated in FIGS. 11-13).

Figure 4:
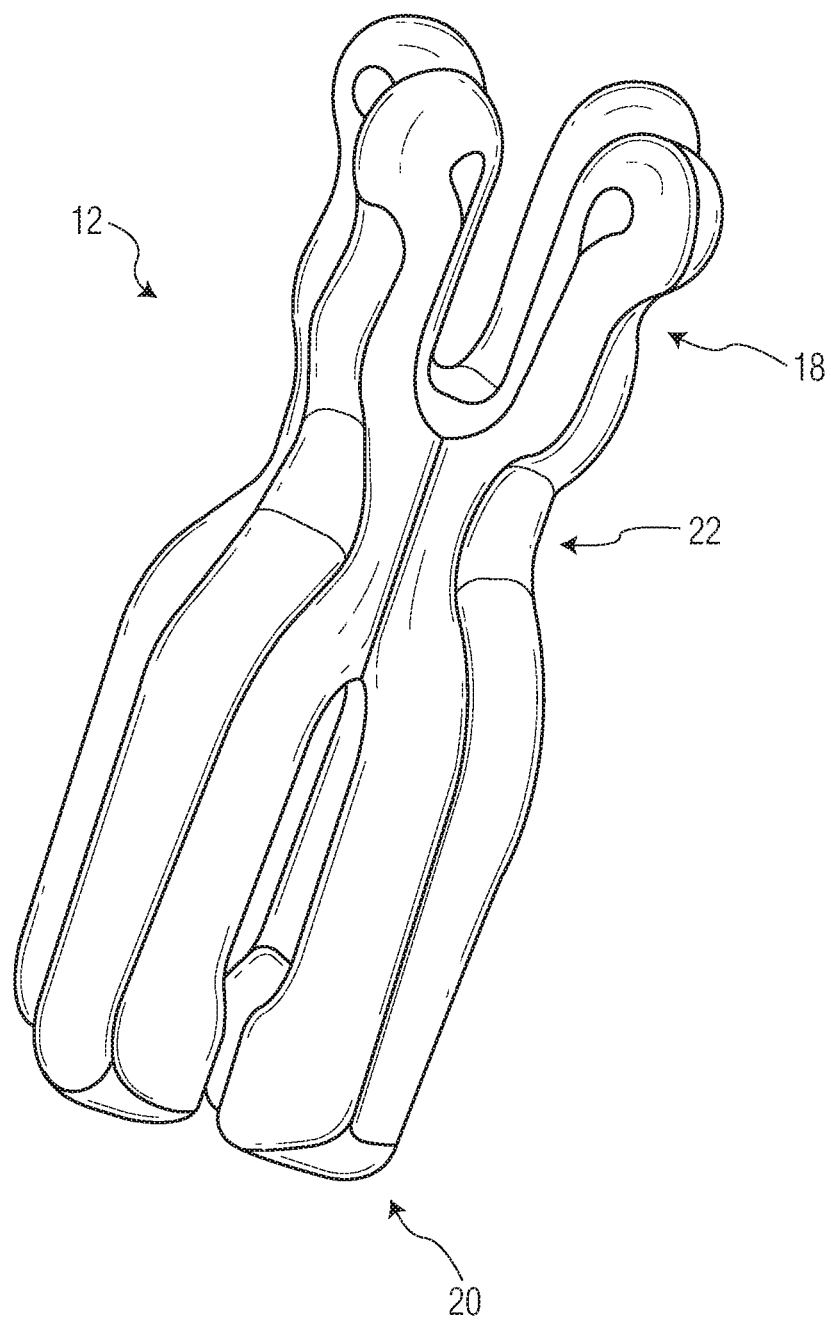

To house the core 12, and resultant vaginal insert 10, in an applicator 40, the core 12 is converted from a radially expanded configuration to an inwardly compressed configuration (such as illustrated in FIG. 4). The inwardly compressed core 12, and resultant vaginal insert 10, can then be loaded into the applicator 40 for storage until such time as needed by a woman. A shortcoming which can be associated with simply placing an inwardly compressed core 12, and resultant vaginal insert 10, into an applicator 40 can be that, as the core 12 of the vaginal insert 10 is under compression, the core 12, and therefore, the vaginal insert 10 can have a tendency to migrate towards the outlet 46 of the applicator 40 such as, for example, during shipping and handling. The migration of the vaginal insert 10 towards the outlet 46 of the applicator 40 can result in premature self-expulsion of the vaginal insert 10 from the applicator 40 or can result in at least partial opening of the petals of the outlet 46 which can result in an uncomfortable insertion experience for the woman attempting to utilize the vaginal insert 10.

The migration of the vaginal insert 10, the at least partial opening of the petals of the outlet 46 of an applicator 40, and/or the self-expulsion of the vaginal insert 10 can be impeded in a variety of ways, such as, but not limited to, stiffening the petals of the outlet 46, narrowing an inside diameter tapering of the housing 42 of the applicator 40 near the outlet 46 of the applicator 40, increasing the surface friction on an inner surface of the housing 42 of the applicator 40 via texturing or other means, altering the topography of the inner surface of the housing 42 of the applicator 40, and/or holding the vaginal insert 10 in place with a physically attached element such as, for example, a string or other means. Packaging elements external to the applicator 40 can also assist in reducing and/or eliminating the drawbacks described. Such packaging elements can include, but are not limited to, blister packaging, using an injection molded cap, a nonwoven sleeve and/or shrinkwrap or other means over the outlet 46 of the applicator 40.

In various embodiments, the core 12 of the vaginal insert 10 can be modified to enable the core 12 to provide an outward force inside the housing 42 of the applicator 40 to retain the vaginal insert 10 inside the housing 42 of the applicator 40 until ready to expel. In various embodiments, any modification made to the core 12 of the vaginal insert 10 can coordinate with the characteristics and/or design of the housing 42 of the applicator 40. Such coordination of the modifications made to the core 12 of the vaginal insert 10 with the characteristics and/or design of the housing 42 of the application 40 can provide for improved interaction between the vaginal insert 10 and the applicator 40 and can reduce and/or eliminate the migration of the vaginal insert 10 through the applicator 40 towards the outlet 46 of the applicator. In various embodiments, the expulsion force required to retain the vaginal insert 10 within the housing 42 of the applicator 40 should be high enough to maintain the vaginal insert 10 enclosed behind the petals of the outlet 46 of the applicator 40 during normal shipping and handling and also allow for ease of expulsion of the vaginal insert 10 from the applicator 40 when needed by a woman. In various embodiments, the expulsion force can range from about 150 to about 4,500 grams force.

In various embodiments, the core 12 of the vaginal insert 10 can be provided with a migration reduction feature. In various embodiments, the core 12 of the vaginal insert 10 can be provided with a plurality of migration reduction features. In various embodiments, the core 12 of the vaginal insert 10 can be provided with at least 1, 2, 3, 4, 5, 6, 7, 8, 9, 10, 11, 12, 13, 14, 15, or 16 migration reduction features. In various embodiments, the migration reduction feature can operate by increasing the friction between the vaginal insert 10 and the inner surface of the housing 42 of the applicator 40. In various embodiments, the migration reduction feature can be located in any location of the core 12 as deemed suitable, such as, for example, an applicator facing surface of the core 12, a non-applicator facing surface of the core 12, or a combination thereof.

A migration reduction feature located on an applicator facing surface of the core 12, such as, for example, an applicator facing surface of the anchoring arms 26 and/or supporting arms 28 of the core 12, can interact, directly or indirectly, with the inner surface of the housing 42 of an applicator 40, such as, for example, a surface texture or an altered topography of the inner surface of the housing 42, to assist in preventing or minimizing the migration of the vaginal insert 10 through the applicator 40. In various embodiments, the migration reduction features can directly interact with the inner surface of the housing 42 of the applicator 40 in such embodiments wherein the migration reduction feature can directly contact the inner surface of the housing 42 of the applicator 40 (e.g., the vaginal insert 10 does not have a cover 14). In various embodiments, the migration reduction feature can interact indirectly with the inner surface of the housing 42 of the applicator 40 in such embodiments wherein the migration reduction feature cannot directly contact the inner surface of the housing 42 of the applicator 40 (e.g., the vaginal insert 10 has a cover 14).

A migration reduction feature positioned on a non-applicator facing surface of the core 12, such as, for example, a non-applicator facing surface of the anchoring arms 26 and/or supporting arms 28 of the core 12, can interact with another migration reduction feature also positioned on a non-applicator facing surface of the core 12, such as, for example, a non-applicator facing surface of the anchoring arms 26 and/or supporting arms 28. The interaction, such as, for example, a pushing of one of the migration reduction features against and away from another of the migration reduction features, can force the arms, such as anchoring arms 26 and/or supporting arms 28, in an outward direction relative to the longitudinal axis 24 of the core 12. The pushing of the anchoring arms 26 and/or supporting arms 28 in an outward direction can result in the application of a force against the inner surface of the housing 42 of the applicator 40 which can prevent or minimize the migration of the vaginal insert 10 through the applicator 40.

In various embodiments, the size dimensions of the migration reduction feature can be designed as deemed suitable to promote interaction between the core 12 of the vaginal insert 10 and the inner surface of the housing 42 of the applicator 40. In various embodiments, the size dimensions of a migration reduction feature positioned on an applicator facing surface of the core 12 can be sized as deemed suitable to promote interaction, direct or indirect, between the migration reduction feature and the inner surface of the housing 42 of the applicator 40. In various embodiments, the size dimensions of a migration reduction feature positioned on a non-applicator facing surface of the core 12 can be sized as deemed suitable to promote interaction between at least two migration reduction features positioned on a non-applicator facing surface of the core 12 within the same element, anchoring 18 or supporting 20, of the core 12.

In various embodiments, the number of, positioning of, and/or size of the migration reduction feature(s) on the core 12 can be designed as deemed suitable to prevent or minimize migration of the vaginal insert 10 within the housing 42 of the applicator 40. While such designs of the migration reduction feature can be made to prevent or minimize migration of the vaginal insert 10 through the applicator 40, such designs should not result in an expulsion force which is too high, thereby, creating difficulty for the user to expel the vaginal insert 10 from the applicator 40 when needed for use. As described herein, the core 12 of the vaginal insert 10 can be made in a variety of size and/or can exhibit a variety of performance characteristics such as Shore A hardness. In various embodiments, the expulsion force for each core 12 and resultant vaginal insert 10, regardless of size and/or exhibited performance characteristic, would be substantially similar.

In various embodiments, a migration reduction feature can be located on an anchoring arm 26 or a supporting arm 28 of a core 12. In various embodiments, such as, for example, in various embodiments wherein more than one migration reduction feature can be present, the plurality of migration reduction features can all be positioned within the anchoring element 18, can all be positioned within the supporting element 20, or combinations thereof, of a core 12. In various embodiments, a migration reduction feature can be located on an applicator 40 facing surface or a non-applicator facing surface of a core 12. In various embodiments, such as, for example, in various embodiments wherein more than one migration reduction feature can be present, the plurality of migration reduction features can all be positioned on an applicator facing surface, can all be positioned on a non-applicator facing surface, or combinations thereof, of a core 12.

In various embodiments, a migration reduction feature can be positioned on an anchoring arm 26 of a core 12. In various embodiments, a migration reduction feature can be located at any position on the anchoring arm 26, such as, for example, closer to the node 22, closer to the anchoring tips 30, or closer to the midpoint of the anchoring arm 26. In various embodiments, a migration reduction feature can be located at substantially an inflection point of the anchoring arm 26 when the core 12 of the vaginal insert 10 is compressed within the housing 42 of the applicator 40. In various embodiments, the size, type, location, material construction, etc of the migration reduction feature can be varied and adjusted dependent upon the size and composition (size dimensions and/or exhibited performance characteristic) of the core 12 of a vaginal insert 10. For example, a core 12 may be designed to have a particular size and exhibit a particular Shore A hardness and the type, size, location and material construction of a migration reduction feature associated with the core 12 can be adjusted based upon the selected size and Shore A hardness of the core 12 in order to prevent or minimize the migration of the vaginal insert 10 in an applicator 40.

As described above, in various embodiments, the migration reduction feature can be positioned on an applicator facing surface of an anchoring arm 26 of the core 12. In such various embodiments, the size, type, material construction, etc. of the migration reduction feature can be varied and adjusted dependent upon a modification made to the inner surface of the housing 42 of the applicator 40. In such various embodiments, the type, size, location and material construction of the migration reduction feature can be sized and adjusted to promote interaction between the migration reduction feature and the inner surface of the housing 42 of the applicator 40 to prevent or minimize migration of the vaginal insert 10 within the housing 42 of the applicator 40.

As described above, in various embodiments, the migration reduction feature can be positioned on a non-applicator facing surface of the core 12. In such various embodiments, the size, type, material construction, etc., of the migration reduction feature can be sized and adjusted such that the migration reduction feature can interact with another migration reduction feature positioned on a non-applicator facing surface of a second anchoring arm 26 of the anchoring element 18 which can result in an application of a force against the inner surface of the housing 42 of an applicator 40 to prevent or minimize migration of the vaginal insert 10 within the housing 42 of the applicator 40.

In various embodiments, a migration reduction feature can be positioned on a supporting arm 28 of a core 12. In various embodiments, a migration reduction feature can be located at any position on the supporting arm 28, such as closer to the node 22, closer to the supporting tips 32, or closer to the midpoint of the supporting arm 28. In various embodiments, a migration reduction feature can be located at substantially an inflection point of the supporting arm 28 when the core 12 of the vaginal insert 10 is compressed within the housing 42 of the applicator 40. In various embodiments, the size, type, location, material construction, etc., of the migration reduction feature can be varied and adjusted dependent upon the size and composition (size dimensions and/or exhibited performance characteristic) of the core 12 of a vaginal insert 10. For example, a core 12 may be designed to have a particular size and exhibit a particular Shore A hardness and the type, size, location, and material construction of a migration reduction feature associated with the core 12 can be adjusted based upon the selected size and Shore A hardness of the core 12 in order to prevent or minimize the migration of the vaginal insert 10 in an applicator 40.

As described above, in various embodiments, the migration reduction feature can be positioned on an applicator facing surface of a supporting arm 28 of the core 12. In such various embodiments, the size, type, material construction, etc. of the migration reduction feature can be varied and adjusted dependent upon a modification made to the inner surface of the housing 42 of the applicator 40. In various embodiments, the type, size, location and material construction of the migration reduction feature can be sized and adjusted to promote interaction between the migration reduction feature and the inner surface of the housing 42 of the applicator 40 to prevent or minimize migration of the vaginal insert 10 within the housing 42 of the applicator 40.

As described above, in various embodiments, the migration reduction feature can be positioned on a non-applicator facing surface of the core 12. In such various embodiments, the size, type, material construction, etc. of the migration reduction feature can be sized and adjusted such that the migration reduction feature can interact with another migration reduction feature positioned on a non-applicator facing surface of a second supporting arm 28 of the supporting element 20 which can result in an application of a force against the inner surface of the housing 42 of an applicator 40 to prevent or minimize migration of the vaginal insert 10 within the housing 42 of the applicator 40.

In various embodiments, a vaginal insert 10 can have a core 12 which can have at least one migration reduction feature located within the anchoring element 18. In various such embodiments, the at least one migration reduction feature can be positioned on an applicator facing surface of at least one anchoring arm 26. In various such embodiments, the at least one migration reduction feature can be positioned on a non-applicator facing surface of at least one anchoring arm 26.

In various embodiments, a vaginal insert 10 can have a core 12 which can have at least two migration reduction features located within the anchoring element 18. In various such embodiments, one of the at least two migration reduction features can be positioned on an applicator facing surface of a first anchoring arm 26 and a second of the at least two migration reduction features can be positioned on an applicator facing surface of a second anchoring arm 26. In various such embodiments, one of the at least two migration reduction features can be positioned on a non-applicator facing surface of a first anchoring arm 26 and a second of the at least two migration reduction features can be positioned on a non-applicator facing surface of a second anchoring arm 26. In various such embodiments, one of the at least two migration reduction features can be positioned on an applicator facing surface of an anchoring arm 26 and a second of the at least two migration reduction features can be positioned on a non-applicator facing surface of an anchoring arm 26 (either the same anchoring arm 26 upon which the first migration reduction feature is positioned or a different anchoring arm 26).

In various embodiments, a vaginal insert 10 can have a core 12 which can have at least one migration reduction feature located within the supporting element 20. In various such embodiments, the at least one migration reduction feature can be positioned on an applicator facing surface of at least one supporting arm 28. In various such embodiments, the at least one migration reduction feature can be positioned on a non-applicator facing surface of at least one supporting arm 28.

In various embodiments, a vaginal insert 10 can have a core 12 which can have at least two migration reduction features located within the supporting element 20. In various such embodiments, one of the at least two migration reduction features can be positioned on an applicator facing surface of a first supporting arm 28 and a second of the at least two migration reduction features can be positioned on an applicator facing surface of a second supporting arm 28. In various such embodiments, one of the at least two migration reduction features can be positioned on a non-applicator facing surface of a first supporting arm 28 and a second of the at least two migration reduction features can be positioned on a non-applicator facing surface of a second supporting arm 28. In various such embodiments, one of the at least two migration reduction features can be positioned on an applicator facing surface of a supporting arm 28 and a second of the at least two migration reduction features can be positioned on a non-applicator facing surface of a supporting arm 28 (either the same supporting arm 28 upon which the first migration reduction feature is positioned or a different supporting arm 28).

In various embodiments, a vaginal insert 10 can have a core 12 which can have at least one migration reduction feature located within the anchoring element 18 and at least one migration reduction feature located within the supporting element 20. In various such embodiments, the at least one migration reduction feature located in the anchoring element 18 and the at least one migration reduction feature located in the supporting element 20 can each be positioned on an applicator facing surface of the core 12. In various such embodiments, the at least one migration reduction feature located in the anchoring element 18 and the at least one migration reduction feature located in the supporting element 20 can each be positioned on a non-applicator facing surface of the core 12. In various such embodiments, one of the at least one migration reduction feature located in the anchoring element 18 and the at least one migration reduction element located in the supporting element 20 can be positioned on an applicator facing surface of the core 12 and the other of the at least one migration reduction feature located in the anchoring element 18 and the at least one migration reduction element located in the supporting element 20 can be positioned on a non-applicator facing surface of the core 12.

In various embodiments, a migration reduction feature can be integral with the core 12 such as, for example, by being molded with the core 12 at the time of manufacture of the core 12. In various embodiments, a migration reduction feature be formed separately from the core 12 and can be bonded with the core 12. The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements. The bonding can occur via adhesive, pressure bonding, thermal bonding, ultrasonic bonding, and/or welding, or any other means deemed suitable.

Figure 18A:
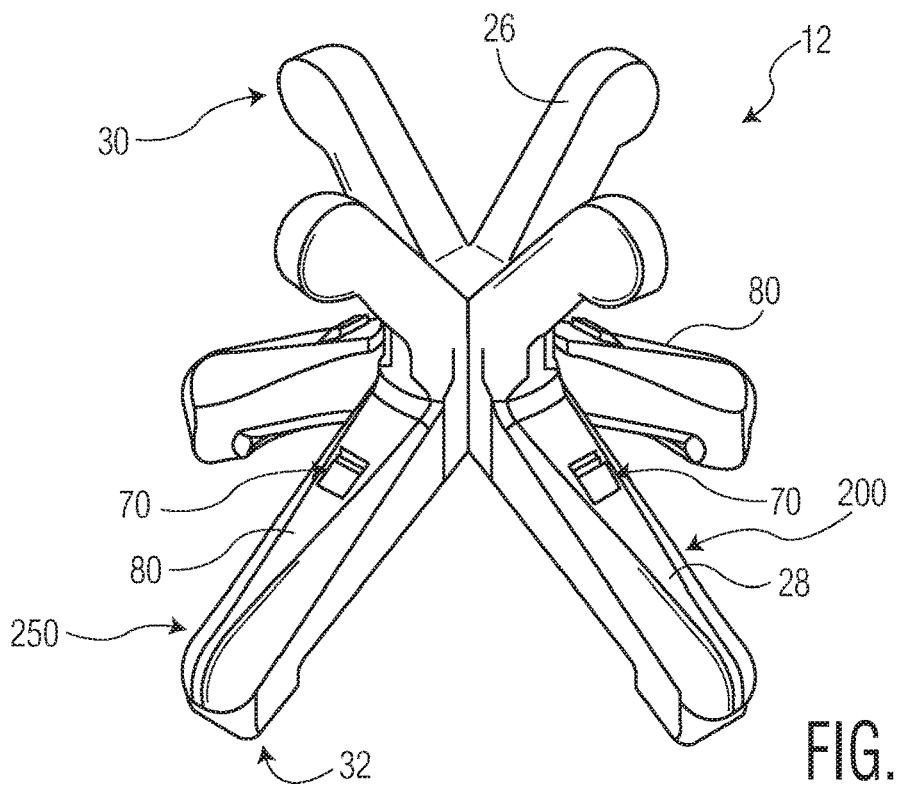
FIG. 18A is a perspective view of an exemplary embodiment of a core.
Figure 18B:
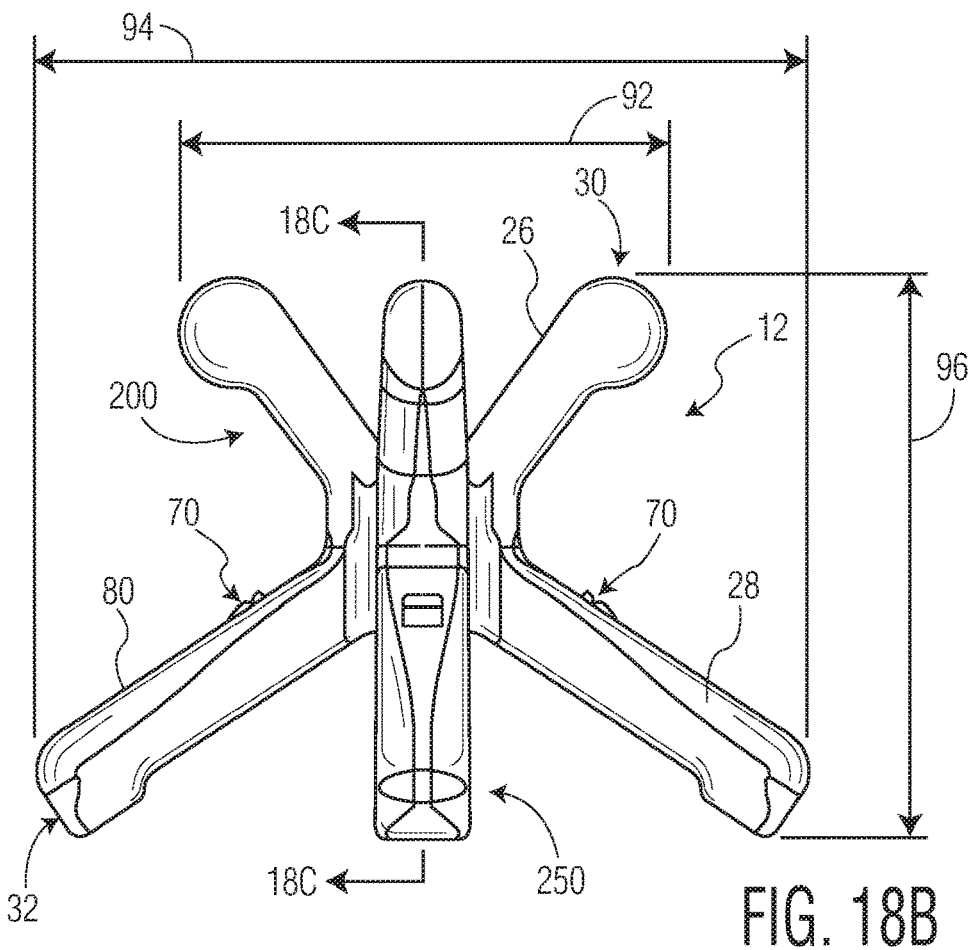
FIG. 18B is a side view of the core of FIG. 18A.
Figure 18C:
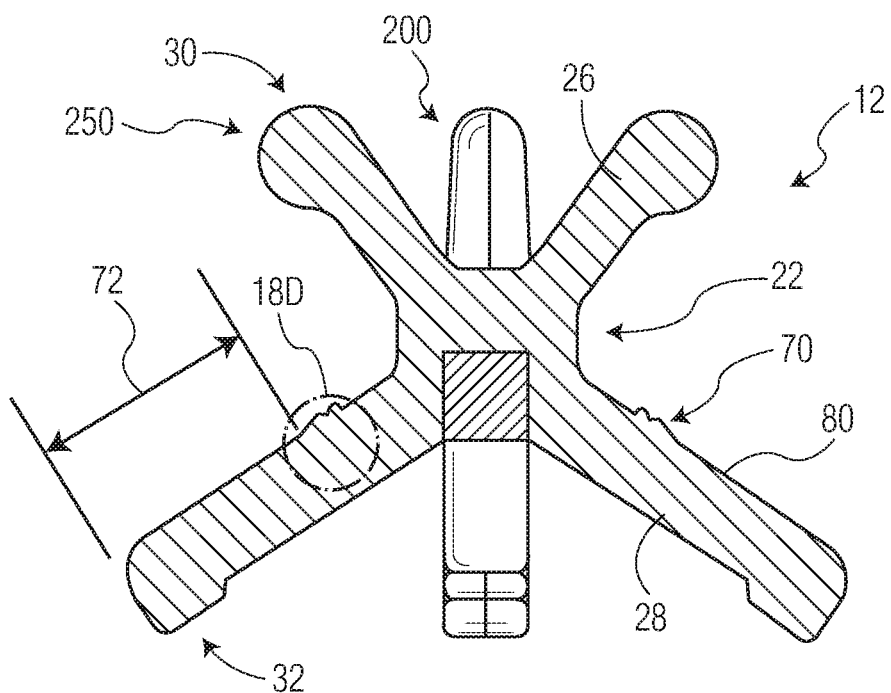
FIG. 18C is a cross-sectional view of the core of FIG. 18B taken along line 18C-18C.

In various embodiments, a migration reduction feature can be located on an applicator facing surface of the core 12. Referring to FIGS. 18A-18D, an illustration of a non-limiting example of an embodiment of at least one migration reduction feature 70 located on an applicator facing surface 80 of the core 12 can be viewed. FIGS. 18A-18D provide exemplary illustrations of an embodiment of two components, 200 and 250, respectively, which can be brought together to form the core 12. The components, 200 and 250, can be formed via any manufacturing method deemed suitable, such as, for example, injection molding the component shape or cutting the component shape out of the chosen construction material. In various embodiments, at least one migration reduction feature 70 can be located on an applicator facing surface 80 of at least one supporting arm 28, at least one anchoring arm 26, or combination thereof, of a core 12. In the exemplary embodiment as illustrated in FIGS. 18A-18D, a migration reduction feature 70 can be located on an applicator facing surface 80 of each of the supporting arms 28 of the core 12. FIG. 18A provides a perspective view of an illustration of a non-limiting example of an embodiment of a migration reduction feature 70 located on an applicator facing surface 80 of each of the supporting arms 28 of a core 12. FIG. 18B provides an illustration of a side view of the core 12 of FIG. 18A. FIG. 18C provides an illustration of a cross-sectional view of the core 12 of FIG. 18B taken along line 18C-18C. In various embodiments, such as when the migration reduction feature 70 can be located on the applicator facing surface 80 of the supporting arms 28, the migration reduction feature 70 can be placed at any distance 72 from the supporting tips 32 as deemed suitable to interact with the inner surface of the housing 42 of an applicator 40 to prevent or minimize migration of the vaginal insert 10 within the housing 42 of an applicator 40. In various embodiments, the distance 72 from the supporting tip 32 to the trailing end 76 (illustrated in FIG. 18D) of the migration reduction feature 70 can be from about 14, 15 or 16 mm to about 17, 18, 19 or 20 mm.

Figure 18D:
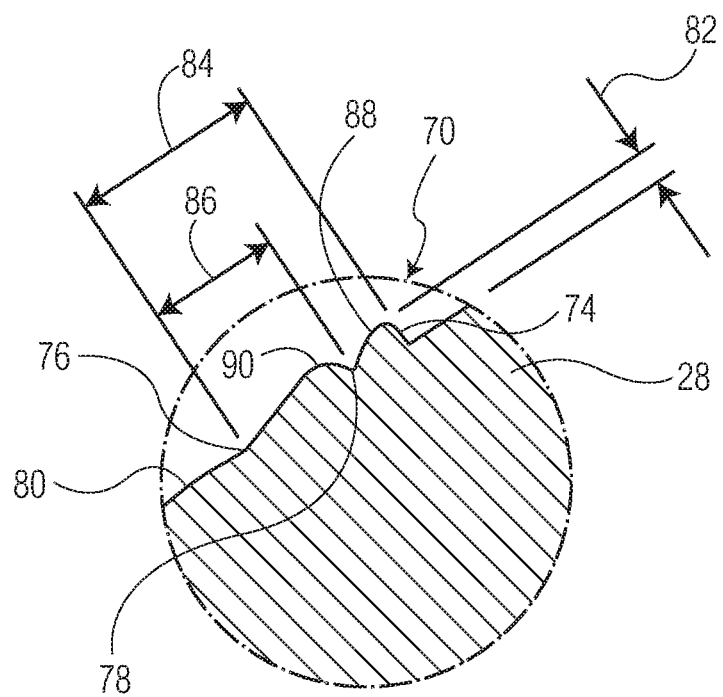
FIG. 18D is a close-up view of Area 18D of FIG. 18C.

FIG. 18D provides a close-up view of the Area 18D of the core 12 of FIG. 18C and provides an illustration of a non-limiting example of a migration reduction feature 70. As illustrated in FIG. 18D, the migration reduction feature 70 can extend outwardly from an applicator facing surface 80 of a supporting arm 28. The migration reduction feature 70 can have a leading end 74 and a trailing end 76. In the embodiment illustrated, the leading end 74 can be the portion of the migration reduction feature 70 which can be closest to the node 22 of the core 12 and which can initiate the outward extension of the migration reduction feature 70 from the applicator facing surface 80 of the core 12. In the embodiment illustrated, the trailing end 76 can be the portion of the migration reduction feature 70 which can be closest to the supporting tips 32 of the core 12 and which can terminate the outward extension of the migration reduction feature 70 from the applicator facing surface 80 of the core 12.

The migration reduction feature 70 can extend outwardly from the applicator facing surface 80 of the core 12 any height 82 as deemed suitable to interact with the inner surface of the housing 42 of the applicator 40 to prevent or minimize migration of the vaginal insert 10. In various embodiments, the height 82 of the migration reduction feature 70, as measured from the applicator facing surface 80 of the core 12 to the outermost extension of the migration reduction feature 70, can be from about 0.20, 0.25, 0.30, 0.40, 0.50, 0.60, 0.70, 0.75, or 0.80 mm to about 0.90, 1.00, 1.10, 1.20, 1.30, 1.40, 1.50 or 1.60 mm.

In various embodiments, the migration reduction feature 70 can contain at least one divot 78 between the leading end 74 and the trailing end 76 of the migration reduction feature 70. The divot 78 can create a reduction in the height 82 of the migration reduction feature 70 (at the location of the divot 78) and, thereby, provide the migration reduction feature 70 with ridges, such as, for example, ridges 88 and 90. In various embodiments, the migration reduction feature 70 can have as many divots 78 and ridges, such as ridges 88 and 90, as deemed suitable. In various embodiments, the migration reduction feature 70 can have no divot 78 and, therefore, can be a single outward extension from the applicator facing surface 80 of the core 12. In various embodiments, the migration reduction feature 70 can have at least 1, 2, 3 or 4 divots 78 and, therefore, can have at least 2, 3, 4, or 5 ridges, such as ridges 88 and 90, extending from the applicator facing surface 80 of the core 12. In various embodiments in which at least two ridges are present in the migration reduction feature 70, each ridge can outwardly extend from the applicator facing surface 80 of the core 12 the same height 82. In various embodiments in which at least two ridges are present in the migration reduction feature 70, a ridge can outwardly extend from the applicator facing surface 80 of the core 12 a height 82 which can differ from the height 82 of another ridge present in the migration reduction feature 70. In various embodiments, the height 82 of a ridge of a migration reduction feature 70 can range from about 0.20, 0.25, 0.30, 0.40, 0.50, 0.60, 0.70, 0.75, or 0.80 mm to about 0.90, 1.00, 1.10, 1.20, 1.30, 1.40, 1.50, or 1.60 mm.

As illustrated in the non-limiting example of an embodiment of a migration reduction feature 70 illustrated in FIG. 18D, the migration reduction feature 70 can have an overall length 84 from the leading end 74 to the trailing end 76. The overall length 84 of the migration reduction feature 70 can be any overall length 84 as deemed suitable and the migration reduction feature 70 can contain as many divots 78 and ridges, such as ridges 88 and 90, within the overall length 84 as deemed suitable. In various embodiments, the overall length 84 of the migration reduction feature 70 can be from about 2.0, 2.5, 3.0, 3.5, or 4.0 mm to about 4.5, 5.0, 5.5, or 6.0 mm. In various embodiments in which the migration reduction feature contains a divot 78, the divot 78 can be located at any location along the overall length 84 of the migration reduction feature 70 as deemed suitable. For example, in an embodiment in which the migration reduction feature 70 has a single divot 78, thereby creating two ridges, such as ridges 88 and 90, the divot 78 can be located halfway between the leading end 74 and the trailing end 76 or can be located closer to either of the leading end 74 or the trailing end 76 as deemed suitable. In the non-limiting embodiment illustrated in FIG. 18D, the divot 78 can be located closer to the leading end 74 of the migration reduction feature 70. In the exemplary embodiment, as the divot 78 can be located closer to the leading end 74 of the migration reduction feature 70, the length 86 between the divot 78 and the trailing end 76 can be more than half of the overall length 84 between the leading end 74 and the trailing end 76 of the migration reduction feature 70. As an example, if the overall length 84 between the leading end 74 and the trailing end 76 of the migration reduction feature can be about 3 mm, the length 86 between the divot 78 and the trailing end 76 can be about 2 mm.

As a non-limiting example, in various embodiments, a core 12 can be made according to the design illustrated in FIGS. 18A-18D and can have the following configuration: The core 12 can be manufactured from a soft silicone polymer and can have a Shore A hardness of 70. The core 12 can have an anchoring element 18, a supporting element 20, and a node 22 located between the anchoring element 18 and the supporting element 20. In the radially expanded configuration, the anchoring element 18 of the core 12 can have a diameter 92 of about 32 mm±1 mm, the supporting element 20 can have a diameter 94 of about 50 mm±1 mm, and the length 96 of the core 12 can be about 37 mm±2 mm. The core 12 can include a migration reduction feature 70 located on the applicator facing surface 80 of each of the supporting arms 28 of the supporting element 20. The migration reduction feature 70 can have a leading end 74 and a trailing end 76 and can have an overall length 84 of about 3 mm from the leading end 74 to the trailing end 76. The distance 72 from the supporting tip 32 to the trailing end 76 can be about 16 mm. The migration reduction feature 70 can include a divot 78, thereby producing two ridges, 88 and 90. The divot 78 can be positioned closer to the leading end 74 of the migration reduction feature 70 and the length 86 between the divot 78 and the trailing end 76 can be more than half of the overall length 84 of the migration reduction feature 70. In this example, the length from the divot 78 to the trailing end 76 can be about 2 mm. Each of the ridges, 88 and 90, can extend from the applicator facing surface 80 of the core 12 to substantially the same height 82 and such height 82 of each ridge can be about 0.5 mm±0.050 mm.

Figure 19A:
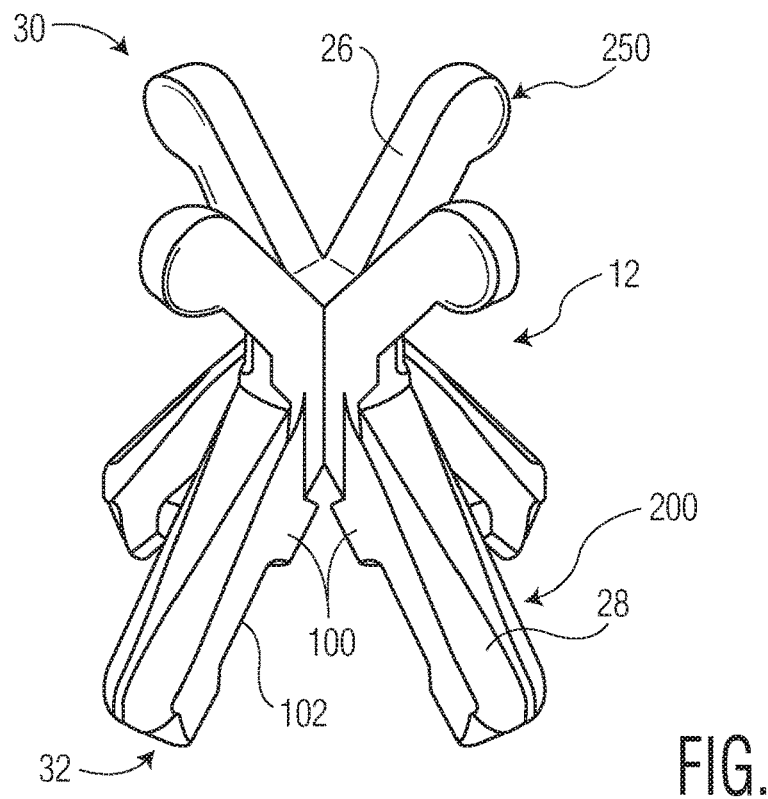
FIG. 19A is a perspective view of an exemplary embodiment of a core.
Figure 19B:
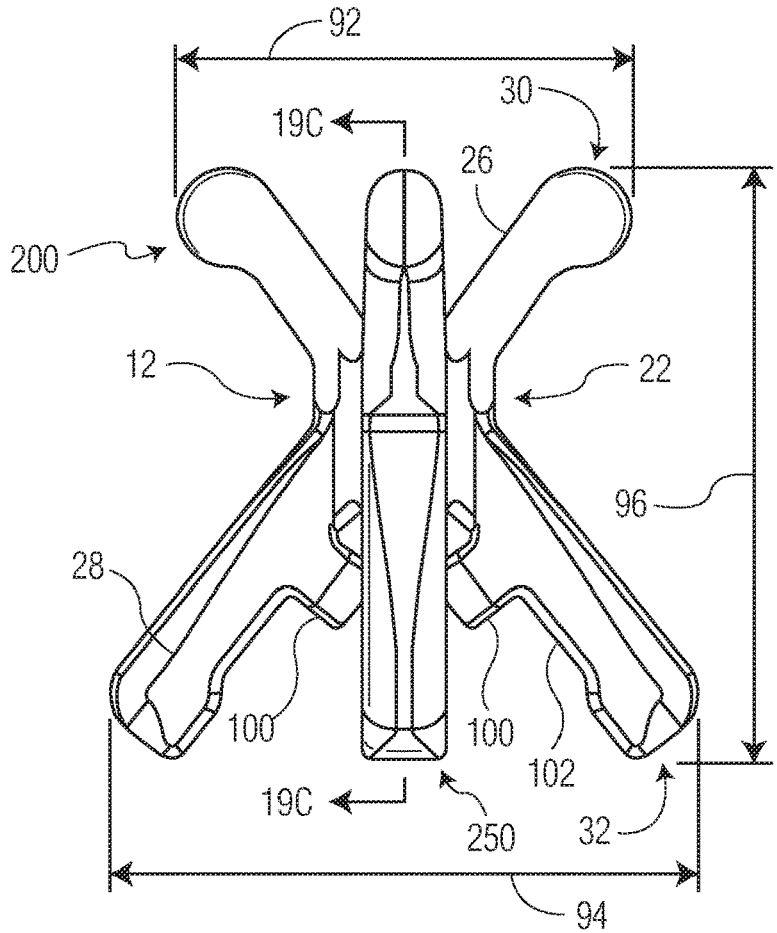
FIG. 19B is a side view of the core of FIG. 19A.
Figure 19C:
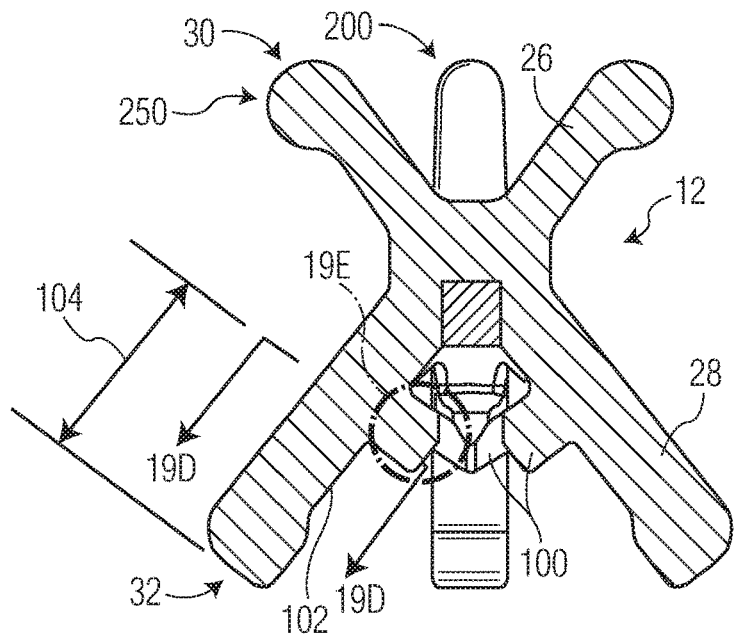
FIG. 19C is a cross-sectional view of the core of FIG. 19B taken along line 19C-19C.

In various embodiments, a migration reduction feature can be located on a non-applicator facing surface of the core 12. Referring to FIGS. 19A-19E, an illustration of a non-limiting example of an embodiment of at least one migration reduction feature 100 located on a non-applicator facing surface 102 of the core 12 can be viewed. FIGS. 19A-19E provide exemplary illustrations of an embodiment of two components, 200 and 250, respectively, which can be brought together to form the core 12. The components, 200 and 250, can be formed via any manufacturing method deemed suitable, such as, for example, injection molding the component shape or cutting the component shape out of the chosen construction material. In various embodiments, at least one migration reduction feature 100 can be located on a non-applicator facing surface 102 of at least one supporting arm 28, at least one anchoring arm 26, or combination thereof, of a core 12. In the exemplary embodiments illustrated in FIGS. 19A-19E, a migration reduction feature 100 can be located on a non-applicator facing surface 102 of each supporting arm 28 of the core 12. FIG. 19A provides a perspective view of an illustration of a non-limiting example of an embodiment of a migration reduction feature 100 located on a non-applicator facing surface 102 of a core 12. FIG. 19B provides an illustration of a side view of the core 12 of FIG. 19A. FIG. 19C provides an illustration of a cross-sectional view of the core 12 of FIG. 19B taken along line 19C-19C. In various embodiments, such as when the migration reduction feature 100 can be located on the non-applicator facing surface 102 of the supporting arms 28, the migration reduction feature 100 can be placed at any distance 104 from the supporting tips 32 as deemed suitable for the core 12 to interact with the inner surface of the housing 42 of an applicator 40 to prevent or minimize migration of the vaginal insert 10 within the housing 42 of an applicator 40. In various embodiments, the distance 104 from the supporting tip 32 to the trailing surface 106 (illustrated in FIG. 19E which is a close-up view of Area 19E of FIG. 19C) of the migration reduction feature 100 can be from about 13, 14, or 15 mm to about 16, 17, or 18 mm.

Figure 19D:
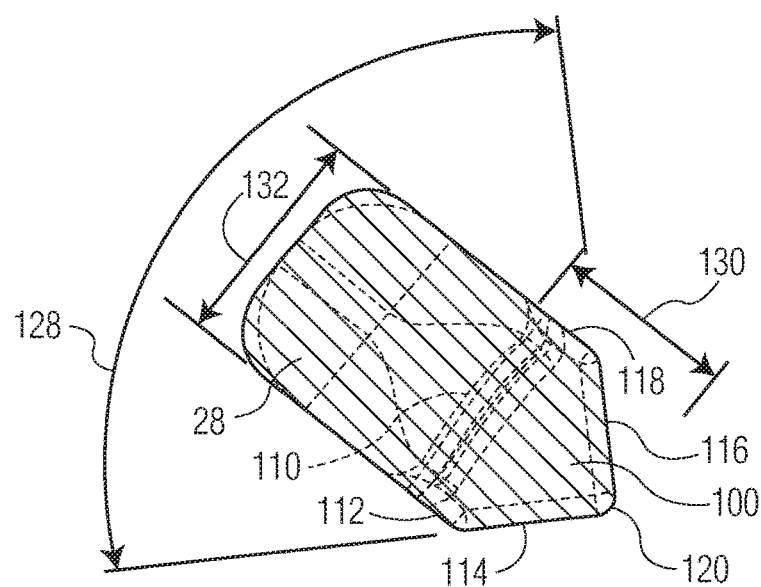
FIG. 19D is a cross-sectional view of the core of FIG. 19C taken along line 19D-19D.
Figure 19E:
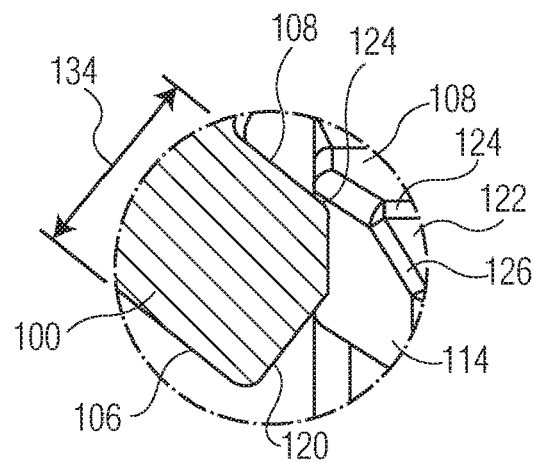
FIG. 19E is a close-up view of Area 19E of the core of FIG. 19C.

FIG. 19D provides a cross-sectional view of the core 12 of FIG. 19C taking along line 19D-19D. As can be seen in the illustration provided, the migration reduction feature 100 can extend from the non-applicator surface 102 of the supporting arm 28. The migration reduction feature 100, as illustrated, can have five sides, such as sides, 110, 112, 114, 116, and 118. Side 110 can abut the non-applicator facing surface 102 of the core 12, sides 112 and 118 can extend perpendicular to the non-applicator facing surface 102 of the core 12, and sides 114 and 116 can extend diagonally from sides 112 and 118, wherein sides 114 and 116 converge towards each other until joining at apex 120. A trailing surface 106 (illustrated in FIG. 19E) can extend between and connect to each of sides 110, 112, 114, 116, and 118, and the apex 120. A leading surface 108 can extend between and connect to each of sides 110, 112, and 118. In various embodiments, the leading surface 108 can also extend between and connect to sides 114 and 116 and apex 120 in addition to extending between and connecting sides 110, 112 and 118 (such as can be illustrated in FIG. 19D). In various embodiments, such as illustrated in FIG. 19E, the leading surface 108 can at least partially connect to sides 114 and 116 but does not fully connect to the apex 120. In such embodiments, the migration reduction feature 100 can have an additional side 122 which can be bounded by edges 124 and a pair of additional edges 126 (one of which is visible in FIG. 19E). Edge 124 can join sides 108 and 122 and the pair of edges 126 can converge towards each other and meet with apex 120.

As illustrated in FIG. 19D, the sides 114 and 116 can converge at apex 120. The angle at which the two sides 114 and 116 converge towards each other can be any angle as deemed suitable. In various embodiments, the angle of convergence 128 of sides 114 and 116 can be about 90°. The migration reduction feature 100 can have an overall length 130, an overall width 132, and an overall height 134. The overall length 130 can be the length from the apex 120 to the side 110 which abuts the non-applicator facing surface 102 of the supporting arm. In various embodiments, the overall length 130 of the migration reduction feature 100 can be from about 1, 2 or 3 mm to about 4, 5, 6 or 7 mm. The overall width 132 of the migration reduction feature 100 can be the width between sides 112 and 118. In various embodiments, the overall width 132 can be from about 1, 2, 3, 4 or 5 mm to about 6 or 7 mm. The overall height 134 can be the distance extending from the leading surface 108 to the trailing surface 106. In various embodiments, the overall height 134 of the migration reduction feature 100 an be from about 1, 2, 3 or 4 mm to about 5, 6 or 7 mm.

As a non-limiting example, in various embodiments, a core 12 can be made according to the design illustrated in FIGS. 19A-19E and can have the following configuration: The core 12 can be manufactured from a soft silicone polymer and can have a Shore A hardness of 50. The core 12 can have an anchoring element 18, a supporting element 20, and a node 22 located between the anchoring element 18 and the supporting element 20. In the radially expanded configuration, the anchoring element 18 of the core 12 can have a diameter 92 of about 32 mm±1 mm, the supporting element 20 can have a diameter 94 of about 41 mm±1 mm, and the length 96 of the core 12 can be about 42 mm±1 mm. The core 12 can include a migration reduction feature 100 located on the non-applicator facing surface 102 of each of the supporting arms 28 of the supporting element 20. The migration reduction feature 100 can be located a distance 104 of about 14.5 mm from the supporting tip 32 to the trailing surface 106 of the migration reduction feature 100. The migration reduction feature 100 can have a leading surface 108 and a trailing surface 106 and an overall height 134 of about 5 mm. The trailing surface 106 can extend between and connect sides, 110, 112, 114, 116, and 118. Side 110 can abut the non-applicator facing surface 102 and sides 114 and 116 can converge towards each other, with an angle of convergence 128 of about 90°, and converge until joining at apex 120. The leading surface 108 can extend between and connect sides 110, 112 and 118 and can partially extend between and connect sides 114 and 116. The migration reduction feature 100 can have an additional side 122 which can be bounded by edge 124 and the pair of edges 126 which can converge until reaching the apex 120. The overall length 130 of the migration reduction feature 100 can be about 4.5 mm and the overall width 132 of the migration reduction 100 feature can be about 6 mm.

Figure 20A:
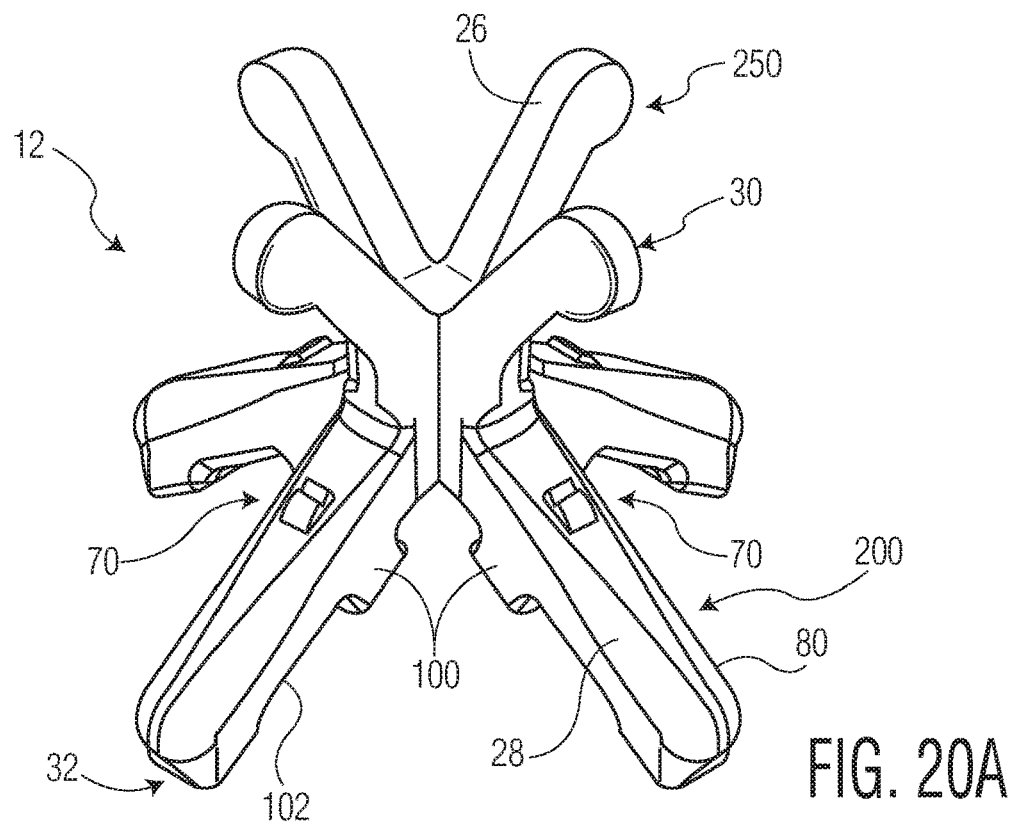
FIG. 20A is a perspective view of an exemplary embodiment of a core.
Figure 20B:
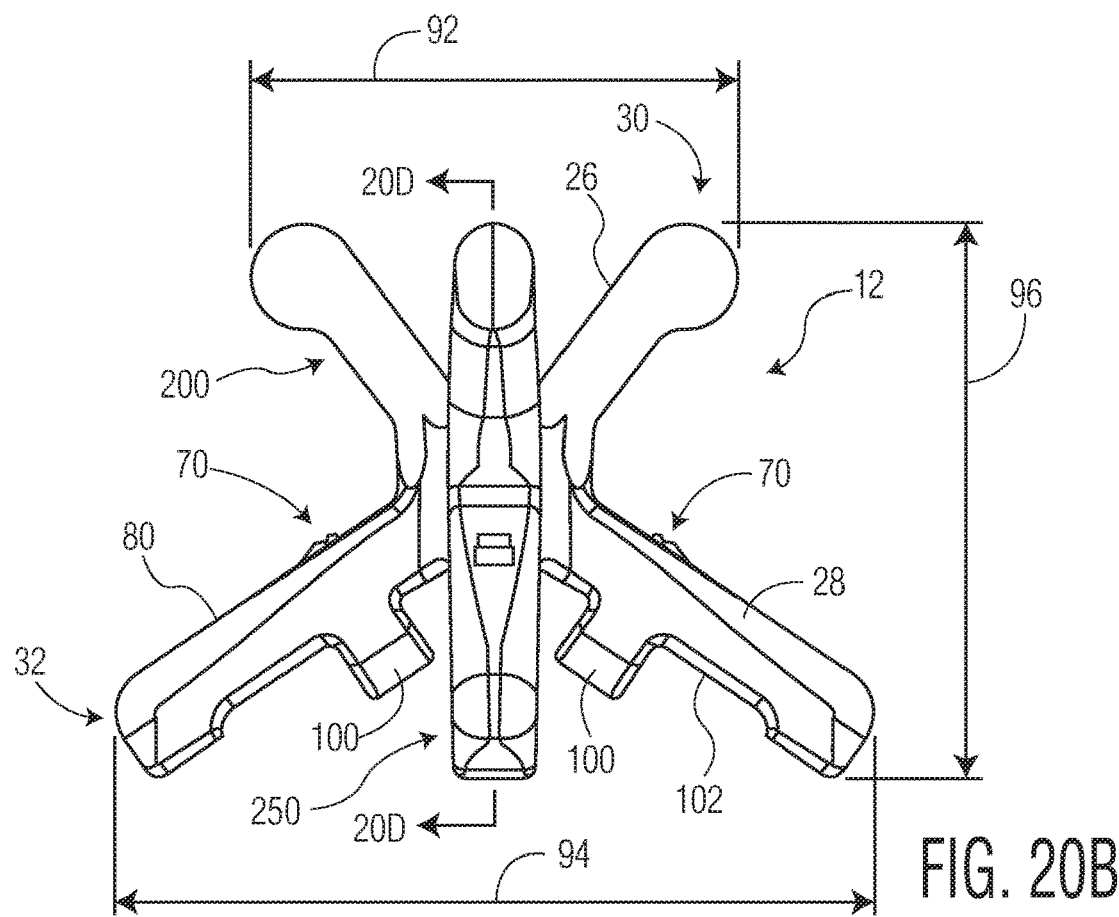
FIG. 20B is a side view of the core of FIG. 20A.
Figure 20C:
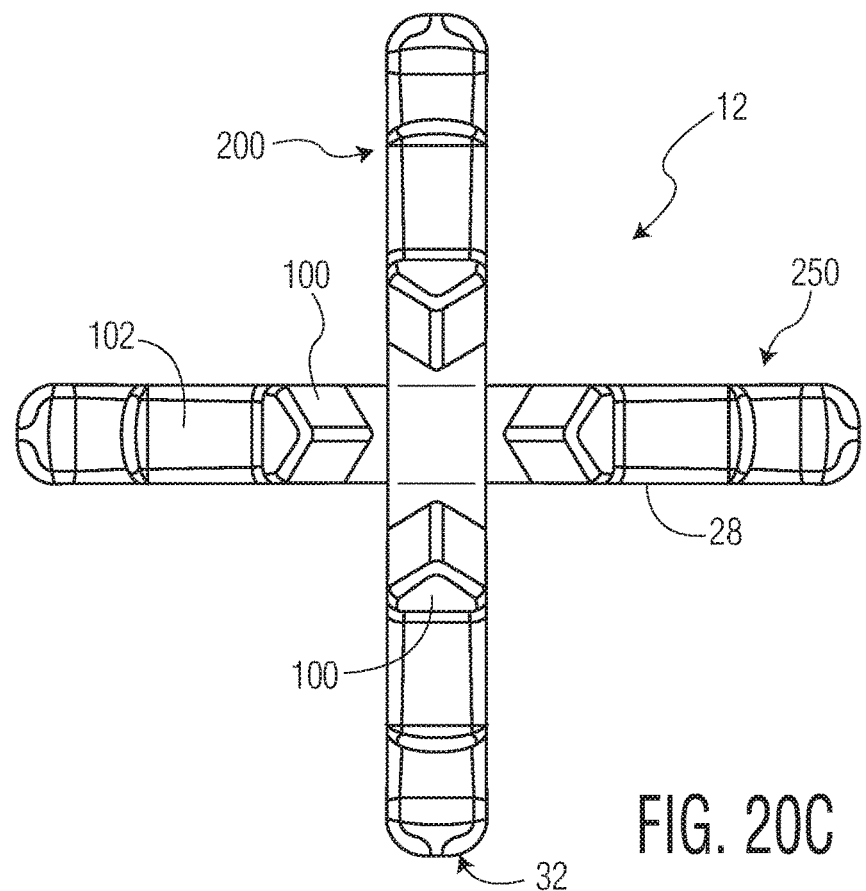
FIG. 20C is a bottom view of the core of FIG. 20A.
Figure 20D:
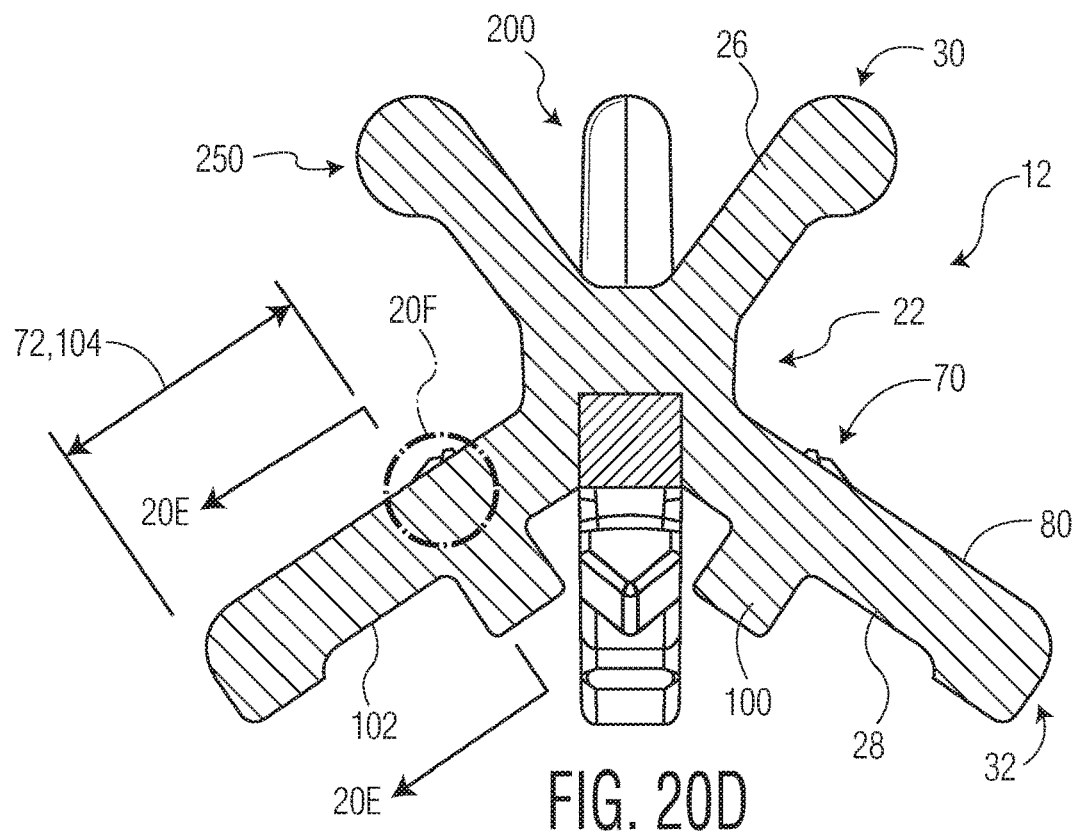
FIG. 20D is a cross-sectional view of the core of FIG. 20B taken along line 20D-20D.
Figure 20E:
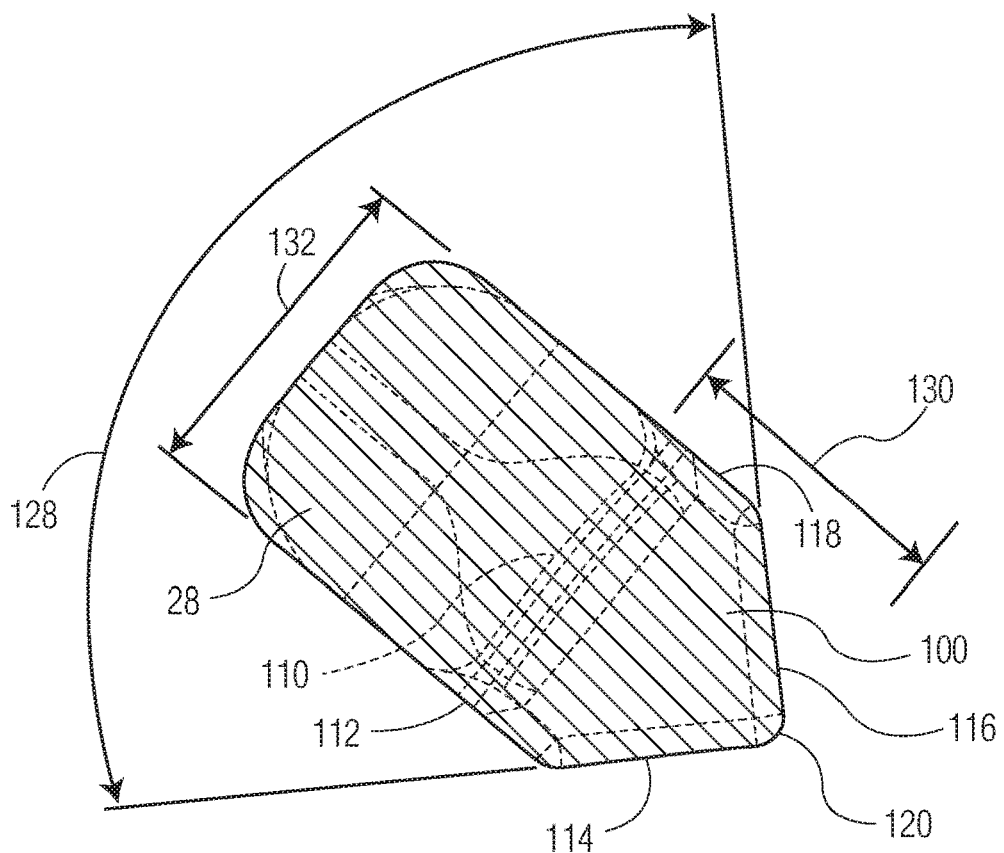
FIG. 20E is a cross-sectional view of the core of FIG. 20D taken along line 20E-20E.
Figure 20F:
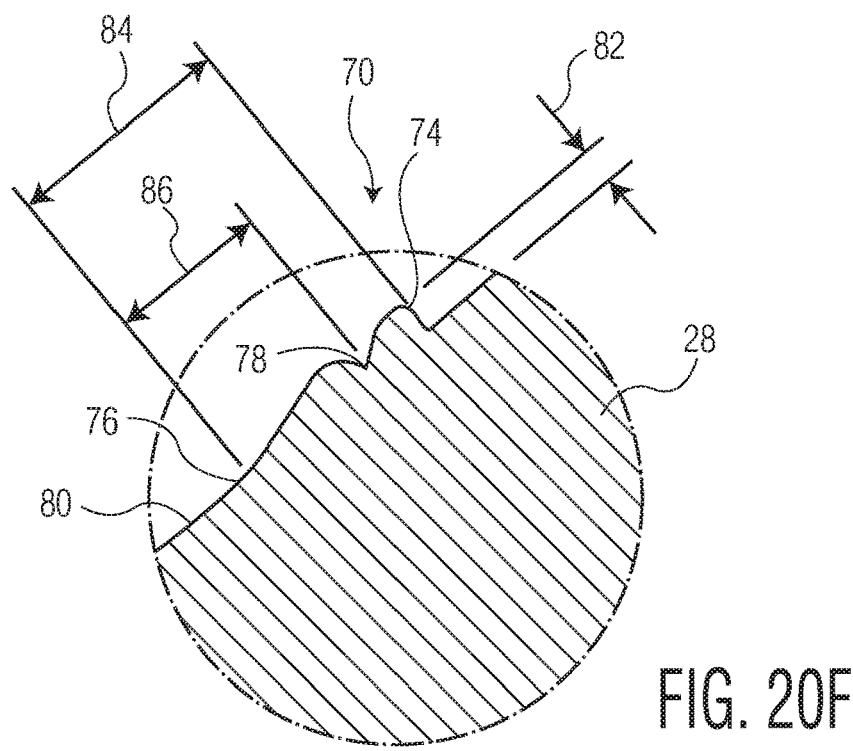
FIG. 20F is a close-up view of Area 20F of the core of FIG. 20D.

In various embodiments, a core 12 can have a migration reduction feature 70 extending from an applicator facing surface 80 of the core 12 and a migration reduction feature 100 extending from a non-applicator facing surface 102 of the core 12. In such embodiments, the migration reduction feature 70 can be as described herein in relation to FIGS. 18A-18D. In such embodiments, the migration reduction feature 100 can be as described herein in relation to FIGS. 19A-19E. Referring to FIGS. 20A-20F, a non-limiting example of an embodiment of a core 12 having at least one migration reduction feature 70 located on an applicator facing surface 80 and at least one migration reduction feature 100 located on a non-applicator facing surface 102 can be illustrated. FIGS. 20A-20F provide exemplary illustrations of an embodiment of two components, 200 and 250, respectively, which can be brought together to form the core 12. The components, 200 and 250, can be formed via any manufacturing method deemed suitable, such as, for example, injection molding the component shape or cutting the component shape out of the chosen construction material. FIG. 20A and FIG. 20B can provide a perspective view and a side view, respectively, of such a core 12 having at least one migration reduction feature 70 located on an applicator facing surface 80 and at least one migration reduction feature 100 located on a non-applicator facing surface 102. FIG. 20C can provide a bottom view of the core 12 and the migration reduction feature 100 extending from the non-applicator facing surface 102 of the core 12. FIG. 20D can provide a cross-section view of the core 12 as illustrated in FIG. 20B and taken along line 20D-20D. FIG. 20E can provide a cross-sectional view of the core 12 illustrated in FIG. 20D and taken along line 20E-20E. FIG. 20F can provide a close-up view of Area 20F of the core 12 illustrated in FIG. 20D.

As a non-limiting example, in various embodiments, a core 12 can be made according to the design illustrated in FIGS. 20A-20F and can have the following configuration: The core 12 can be manufactured from a soft silicone polymer and can have a Shore A hardness of 50. The core 12 can have an anchoring element 18, a supporting element 20, and a node 22 located between the anchoring element 18 and the supporting element 20. In the radially expanded configuration, the anchoring element 18 of the core 12 can have a diameter 92 of about 32 mm±1 mm, the supporting element 20 can have a diameter 94 of about 50 mm±1 mm, and the length 96 of the core 12 can be about 37 mm±2 mm. The core 12 can include a migration reduction feature 70 located on the applicator facing surface 80 of each of the supporting arms 28 of the supporting element 20. The migration reduction feature 70 can have a leading end 74 and a trailing end 76 and can have an overall length 84 of about 3 mm from the leading end 74 to the trailing end 76. The distance 72 from the supporting tip 32 to the trailing end 76 can be about 16 mm. The migration reduction feature 70 can include a divot 78, thereby producing two ridges, 88 and 90. The divot 78 can be positioned closer to the leading end 74 of the migration reduction feature 70 and the length 86 between the divot 78 and the trailing end 76 can be more than half of the overall length 84 of the migration reduction feature 70. In this example, the length from the divot 78 to the trailing end 76 can be about 2 mm. Each of the ridges, 88 and 90, can extend from the applicator facing surface 80 of the core 12 to substantially the same height 82 and such height 82 of each ridge can be about 0.50 mm±0.05 mm. The core 12 can include a migration reduction feature 100 located on the non-applicator facing surface 102 of each of the supporting arms 28 of the supporting element 20. The migration reduction feature 100 can be located a distance 104 of about 16 mm from the supporting tip 32 to the trailing surface 106 of the migration reduction feature 100. The migration reduction feature 100 can have a leading surface 108 and a trailing surface 106 and an overall height 134 of about 5 mm. The leading surface 108 and the trailing surface 106 can extend between and connect sides, 110, 112, 114, 116, and 118. Side 110 can abut the non-applicator facing surface 102 and sides 114 and 116 can converge towards each other, with an angle of convergence 128 of about 90°, and converge until joining at apex 120. The overall length 130 of the migration reduction feature 100 can be about 5 mm and the overall width 132 of the migration reduction feature 100 can be about 6 mm.

In various embodiments, a core 12 can be designed as deemed suitable. As described herein, a core 12 can have an anchoring element 18, a supporting element 20, and a node 22 connecting the anchoring element 18 and the supporting element 20. The core 12 can be designed in a variety of sizes wherein the difference between one size of a core 12 and another size of a core 12 can be in any one of the following: the diameter 92 of the anchoring element 18 when in a radially expanded configuration; the diameter 94 of the supporting element 20 when in a radially expanded configuration; the length 96 of the core 12 when the core 12 is in an expanded configuration; the Shore A hardness of the core 12; the presence, if desired, of a migration reduction feature 70 on an applicator facing surface 80 of the core 12; the presence, if desired, of a migration reduction feature 100 on a non-applicator facing surface 102 of the core 12.

In various embodiments, a core 12 can be designed as deemed suitable and can have an anchoring element 18 which can have a diameter from about 30 to about 33 mm when in a radially expanded configuration; a supporting element 20 which can have a diameter from about 34 to about 52 mm when in a radially expanded configuration; a length from about 34 to about 46 mm when in an expanded configuration; a Shore A hardness from 30-80; optionally, a migration reduction feature 70 positioned on an applicator facing surface 80 of the core 12; optionally, a migration reduction feature 100 positioned on a non-applicator facing surface 102 of the core 12; optionally, both of a migration reduction feature 70 positioned on an applicator facing surface 80 of the core 12 and a migration reduction feature 100 positioned on a non-applicator facing surface 102 of the core 12. In such various embodiments wherein a migration reduction feature, such as migration reduction features 70 and/or 100, are located on the core 12, the number of, size of and placement of such migration reduction features can be designed as deemed suitable. In various embodiments, the length 84 of a migration reduction feature 70 can be from about 2.0 mm to about 6.0 mm and the height 82 of a migration reduction feature 70 can be from about 0.02 mm to about 1.60 mm. In various embodiments, the length 130 of a migration reduction feature 100 can be from about 1 to about 7 mm; the width 132 of a migration reduction feature 100 can be from about 1 to about 7 mm; the height 134 of a migration reduction feature 100 can be from about 1 to about 7 mm.

In various embodiments, an array of at least two vaginal inserts 10 which can have different sizes of cores 12 can be provided. A woman may find such an array in a single common outer package or one vaginal insert 10 with one size of core 12 may be in a first package and a vaginal insert 10 with a different size of core 12 may be in a second package, and the two packages may be located in the vicinity of each other, such as in the same shopping aisle of a store. In various embodiments, the array of vaginal inserts 10 can have at least one vaginal insert 10 having one size of core 12 with at least one migration reduction feature (70 and/or 100) and another vaginal insert 10 having a different size of core 12 with at least one migration reduction feature (70 and/or 100). In such embodiments, the sizes of cores 12 can differ from each other in at least one of, for example, exhibiting a different performance characteristic, material hardness, operational dimension, weight, overall diameter of the supporting element 20 of the core 12 when the supporting arms 28 are radially expanded, and/or the radial spread angle at which the supporting arms 28 protrude outwardly relative to the longitudinal axis 24 of the core 12 and/or type of migration reduction feature.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. A vaginal insert comprising a core, the core comprising:
   a. a first component comprising:
      i. a first major surface and a second major surface separated from the first major surface by a first thickness;
      ii. a first anchoring arm and a second anchoring arm;
      iii. a first supporting arm and a second supporting arm;
      iv. a first intermediate region separating the first and second anchoring arms from the first and second supporting arms; and
      v. a first groove within the first intermediate region, the first groove extending between and connecting the first and second anchoring arms;
      vi. a first edge proximal to a junction between the first groove and the first anchoring arm;
      vii. a second edge proximal to a junction between the first groove and the second anchoring arm;
      viii. a first width dimension between the first edge and the second edge;
   b. a second component comprising:
      i. a third major surface and a fourth major surface separated from the third major surface by a second thickness;
      ii. a third anchoring arm and a second anchoring arm;
      iii. a third supporting arm and a second supporting arm;
      iv. a second intermediate region separating the third and fourth anchoring arms from the third and fourth supporting arms; and
      v. a second groove within the second intermediate region, the second groove extending between and connecting the third and fourth supporting arm;
      vi. a third edge proximal to a junction between the second groove and the third supporting arm;
      vii. a fourth edge proximal to a junction between the second groove and the fourth supporting arm;
      viii. a second width dimension between the third edge and the fourth edge;
      wherein the first intermediate region of the first component fits within the second groove of the second component and the second intermediate region of the second component fits within the first groove of the first component, and wherein the first width dimension is smaller than the second thickness and the second width dimension is smaller than the first thickness.

2. The vaginal insert of claim 1 wherein the first width dimension is from 10% to 90% smaller than the second thickness.

3. The vaginal insert of claim 1 wherein the second width dimension is from 10% to 90% smaller than the first thickness.

4. The vaginal insert of claim 1 further comprising a cover.

5. The vaginal insert of claim 1 further comprising a removal element.

6. The vaginal insert of claim 1 wherein the core further comprises a first migration reduction feature located on the first supporting arm of the first component.

7. The vaginal insert of claim 6 wherein the first migration reduction feature is located on an applicator facing surface of the first supporting arm of the first component.

8. The vaginal insert of claim 6 wherein the first migration reduction feature is located on a non-applicator facing surface of the first supporting arm of the first component.

9. The vaginal insert of claim 6 further comprising a second migration reduction feature located on an applicator facing surface of the first supporting arm of the first component.

10. The vaginal insert of claim 6 further comprising a second migration reduction feature located on a non-applicator facing surface of the first supporting arm of the first component.

11. The vaginal insert of claim 6 further comprising a second migration reduction feature located on the second supporting arm of the first component.

* * * * *